United States Patent [19]
Maiti et al.

[11] Patent Number: 5,686,441
[45] Date of Patent: Nov. 11, 1997

[54] PENAM SULFONES AS β-LACTAMASE INHIBITORS

[75] Inventors: Samarendra Nath Maiti; Oludotun Adebayo Phillips; Andhe Venkat Narender Reddy; Eduardo Luis Setti, all of Edmonton; Ronald George Micetich, Sherwood Park, all of Canada; Chieko Kunugita, Tokushima-ken, Japan; Fusahiro Higashitani, Tokushima, Japan; Akio Hyodo, Tokushima-ken, Japan

[73] Assignees: Synphar Laboratories, Inc., Alberta, Canada; Taiho Pharmaceutical Co., Ltd., Tokyo-to, Japan

[21] Appl. No.: 511,227

[22] Filed: Aug. 4, 1995

[51] Int. Cl.$^6$ .................... C07D 499/08; C07D 499/00; A61K 31/43

[52] U.S. Cl. .............................. 514/195; 540/310

[58] Field of Search ............................. 540/310; 514/195

[56] References Cited

U.S. PATENT DOCUMENTS

| | | | |
|---|---|---|---|
| 4,234,579 | 11/1980 | Barth | 424/246 |
| 4,562,073 | 12/1985 | Micetich et al. | 424/114 |

FOREIGN PATENT DOCUMENTS

| | | |
|---|---|---|
| 0503 597 A2 | 11/1992 | European Pat. Off. . |
| 0640 601 A1 | 12/1994 | European Pat. Off. . |
| 63-66187 | 3/1988 | Japan . |

OTHER PUBLICATIONS

Gottstein et al., *J. Med. Chem.*, "Synthesis and β–Lactamase Inhibitory Properties of 2β–(Chloromethyl)–2α–methylpenam–3α–carboxylic Acid 1,1–Dioxide", vol. 24, No. 12, pp. 1531–1534 (1981).

Gottstein et al., *J. Med. Chem.*, "Synthesis and β–Lactamase Inhibitory Properties of 2β–[(Acyloxy)methyl]–2–methylpenam–3α–carboxylic Acid 1,1–Dioxides", vol. 28, No. 4, pp. 518–522 (1985).

Tanaka et al., *J. Antibiotics*, "Synthesis and β–Lactamase Inhibitory Properties of 2β–(Thio–Substituted Methyl)–Penam 1, 1–Dioxides", vol. XLI, No. 4, pp. 579–582 (1988).

Poster No. 147, ICAAC, Oct. 4–7, 1994, Orlando, Florida.
Poster No. 149, ICAAC, Oct. 4–7, 1994, Orlando, Florida.
Poster No. 151, ICAAC, Oct. 4–7, 1994, Orlando, Florida.
Poster No. 153, ICAAC, Oct. 4–7, 1994, Orlando, Florida.
Poster No. 155, ICAAC, Oct. 4–7, 1994, Orlando, Florida.

Lunn and Hipskind; Tetrahedron Letters; The International Journal for the Rapid Publication of Preliminary Communications in Organic Chemistry; Oct. 13, 1992; vol. 33, No. 42 pp. 6291–6294.

*Primary Examiner*—Mukund J. Shah
*Assistant Examiner*—King Lit Wong
*Attorney, Agent, or Firm*—Nikaido, Marmelstein, Murray & Oram LLP

[57] ABSTRACT

Novel 3-(substituted)-3-methyl-4-thia-1-azabicyclo[3.2.0] heptane-2-carboxylate, 4,4-dioxides which are of value for use in combination with β-lactam antibiotics to increase the effectiveness of the antibiotics.

14 Claims, No Drawings

PENAM SULFONES AS β-LACTAMASE INHIBITORS

BACKGROUND OF THE INVENTION

This invention relates to novel 3-(substituted)-3-methyl-4-thia-1-azabicyclo[3.2.0]heptane-2-carboxylate, 4,4-dioxides which are of value for use in combination with β-lactam antibiotics to enhance the effectiveness of the antibiotic.

Of all the commercially available β-lactam antibiotics, penicillins and cephalosporins are well known antibiotics and are most frequently used in the therapy. Although these agents are widely used as useful chemotherapeutic agents, enzymatic inactivation of β-lactam antimicrobial agents has been an obstacle to the treatment of bacterial infection for as long as these agents have been used. The production of enzymes that degrade the β-lactam ring containing antimicrobial agents—penicillins and cephalosporins—causing the antibiotic to lose its antimicrobial activity is the most critical mechanism of bacterial resistances. A novel approach to countering these bacterial enzymes is the delivery of a β-lactam antimicrobial agent combined with an inhibitor against these enzymes. When a β-lactamase inhibitor is used in combination with a penicillin or cephalosporin it can enhance the antibacterial effectiveness of these penicillins or cephalosporins against β-lactamase producing microorganisms.

The present invention provides certain novel penicillin derivatives which have potent bacterial β-lactamase inhibitory activity. More specifically, these new chemical substances are derivatives of penicillanic acid, certain salts and esters thereof.

Penam sulfone (sulbactam) is a known β-lactamase inhibitor (U.S. Pat. No. 4,234,579); 2β-(triazolylmethyl) penicillanic acid derivatives (U.S. Pat. No. 4,562,073) and 2α-(triazolylmethyl) penicillanic acid derivatives (JP 66187/1988) are also potent-β-lactamase inhibitors. Several publications from Bristol-Myers (J. Med. Chem., 24, 1531, 1981 and J. Med. Chem., 28, 518, 1985) refer to 2-(substituted methyl) penam sulfones allegedly having β-lactamase inhibitory properties. Another report described the synthesis and β-lactamase inhibitory properties of 2β-(thiosubstituted methyl) penam sulfones (J. Antibiot., 41, 579, 1988). Several posters from Hoffman-La Roche (posters no. F-147, F-149, F-151, F-153 and F-155, presented at ICAAC, Oct. 4–7, 1994, Orlando, USA) described β-alkenyl penam sulfones as potent β-lactamase inhibitors.

SUMMARY OF THE INVENTION

It is an object of the present invention to provide novel and new penam sulfone derivatives having β-lactamase inhibitory action.

It is another object of the invention to provide processes for preparing the same.

It is a further object of the invention to provide pharmaceutical compositions comprising a β-lactamase inhibitor of this invention in combination with a β-lactam antibiotic and a pharmaceutically-acceptable carrier or diluent.

It is an additional object of the invention to provide an improved method for the treatment of bacterial infections caused by β-lactamase producing bacteria in mammalian subjects.

Accordingly, this invention provides novel 3-(substituted) -3-methyl-4-thia-1-azabicyclo[3.2.0]heptane-2-carboxylate, 4,4-dioxide derivatives selected from the group consisting of

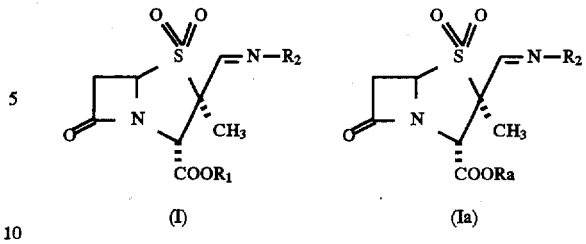

compounds of formulas I and Ia, the pharmaceutically-acceptable salts thereof and the pharmaceutically-acceptable esters thereof, which are readily hydrolyzable in vivo, wherein $R_1$ is a carboxy protecting group acceptable in the synthesis of penicillin derivatives; $R_a$ is hydrogen or a pharmaceutically-acceptable salt forming agent or a pharmaceutically acceptable ester residue which is easily hydrolyzed in vivo and which is a non-poisonous ester capable of rapidly hydrolyzing in the blood or tissue of humans, thereby producing the corresponding acid of the formula (Ia) in which $R_a$ is hydrogen atom.

Also, included with the scope of this invention are compounds of the formulas I and Ia, wherein $R_2$ is selected from $OR_3$ or $NR_4R_5$.

The compounds of formula (I) wherein $R_3$ is hydrogen, are useful as intermediates to the β-lactamase inhibitors of this invention.

Preferably, the beta-lactamase inhibitors of the invention of formula Ia are acidic ($R_a$=H) and they will form salts with basic agents. All such salts are considered to be within the scope of this invention, although for the purpose of administering a salt of a compound of formula Ia to a mammalian subject, it is necessary to use a pharmaceutically-acceptable non-toxic salt.

DETAILED DESCRIPTION OF THE INVENTION

The β-lactamase inhibitors of this invention are the compounds of formulas I & Ia.

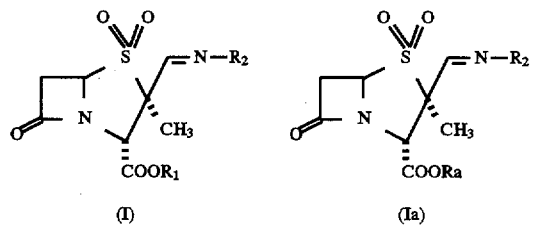

The β-lactamase inhibitors of the invention are effective in enhancing the antimicrobial activity of β-lactam antibiotics, when used in combination with the β-lactam antibiotic to treat a mammalian subject suffering from a bacterial infection caused by a β-lactamase producing microorganism. Examples of antibiotics which can be used in combination with the compounds of the present invention are commonly used penicillins, such as amoxicillin, ampicillin, azlocillin, mezlocillin, apalcillin, hetacillin, bacampicillin, carbenicillin, sulbenicillin, ticarcillin, piperacillin, mecillinam, methicillin, ciclacillin, talampicillin, and commonly used cephalosporins, such as cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, ceftazidime, cefpiramide, ceftriaxone, cefbuperazone, and salts thereof.

$R_1$ in the formula (I) is the residue of a carboxy protecting group. A variety of protecting groups conventionally used in the penicillin art to protect carboxy groups can be used for $R_1$. The major requirements for the protection group is that it can be removed without cleaving the β-lactam ring, and is sufficiently stable under the reaction conditions to permit easy access to the compound of formula (Ia) by the methods described in this invention. Examples of the most commonly used ester-protecting groups are: benzyl, diphenylmethyl, 4-nitrobenzyl, 4-methoxybenzyl, allyl, t-butyl, methoxymethyl, tetrahydropyranyl, 2,2,2-trichloroethyl, trimethylsilyl, etc.

This invention also includes the pharmaceutically acceptable esters of the compounds of formula (Ia) which are readily hydrolyzed in vivo. These types of esters are now quite conventional for penicillanic acid compounds. In general, these esters are cleaved easily under physiological conditions producing the non-toxic pharmaceutically acceptable free acid of the formula (Ia) in which $R_a$ is hydrogen atom. In many instances, formation of such an ester from a carboxylic acid improves the oral absorption of the parent acid. U.S. Pat. No. 4,446,144 and EP 13,617 describes a number of ester-forming radicals which give pharmaceutically acceptable esters readily hydrolyzable in vivo. Examples of the group for forming a readily in vivo hydrolyzable ester groups represented by $R_a$ in the formula (Ia) include: 3-phthalidyl, 4-crotonolactonyl, and gamma-butyrolacton-4-yl, and the like. Preferred individual esters readily hydrolyzable in vivo of the β-lactamase inhibitors of formula (Ia) are the pivaloyloxymethyl and (1-ethoxycarbonyloxy) ethyl esters.

Examples of the group for forming a pharmaceutically acceptable salt represented by $R_a$ in the formula (Ia) include the inorganic base salts, ammonium salts, organic base salts, basic amino acid salts, inorganic acid addition salts, and organic acid addition salts. Inorganic bases that can form the inorganic base salts include alkali metals (e.g., sodium, potassium, and lithium) and alkaline earth metals (e.g., calcium and magnesium). Organic bases that can form the organic base salts include n-propylamine, n-butylamine, cyclohexylamine, benzylamine, octylamine, ethanolamine, diethanolamine, diethylamine, triethylamine, dicyclohexylamine, procaine, choline, N-methylglucamine, morpholine, pyrrolidine, piperidine, N-ethylpiperidine, and N-methylmorpholine. Basic amino acids that can form the basic amino acid salts include lysine, arginine, ornithine and histidine.

As will be appreciated by one skilled in the art, the compounds of formula (Ia) containing a basic nitrogen atom are capable of forming acid addition salts. Such salts with pharmaceutically acceptable acids are included in the invention. Examples of such acids are hydrochloric, hydrobromic, phosphoric, sulfuric, citric, oxalic, maleic, fumaric, tartaric, succinic, malic, formic, acetic, trifluoroacetic, methanesulfonic, trifluoromethanesulfonic, benzenesulfonic, p-toluene sulfonic, 2-naphthalenesulfonic, and the like.

Moreover, when $R_a$ is hydrogen in the formula (Ia) it can form a zwitterion by interacting with a basic nitrogen atom present in the same molecule.

$R_2$ of formulas I & Ia above represents $OR_3$, wherein $R_3$ represents:

(a) hydrogen;
(b) straight or branched chain alkyl having from 1 to 20 carbon atoms;
(c) alkenyl having from 2 to 20 carbon atoms;
(d) alkynyl having from 2 to 20 carbon atoms;
(e) cycloalkyl having from 3 to 8 carbon atoms;
(f) cycloalkenyl having from 5 to 8 carbon atoms;
(g) aryl having from 6 to 10 carbon atoms;
(h) aralkyl wherein alkyl and aryl are as previously defined;
(i) a heterocyclic group including heterocyclic alkyl wherein the heterocyclic group means a 5-(or 6-) membered ring containing from 1 to 4 of any one or more of the heteroatoms selected from O, S and N. Preferred heterocyclic rings include thienyl, furyl, pyridyl, triazolyl, thiadiazolyl, tetrazolyl, piperidinyl, and the like.

The above groups (b) to (i) can be unsubstituted or substituted by radicals such as alkyl, hydroxy, alkoxy, alkanoyloxy, halo, cyano, azido, nitro, carboxy, alkoxycarbonyl, alkanoyl, amino, substituted amino, amidino, guanidino, carboxamido, substituted carboxamido, mercapto, sulfinyl, sulfonyl, diethoxyphosphinylalkyl, dihydroxyphosphinylalkyl, a heteroarylthio, a heteroaryl group bonded via carbon, or a nitrogen containing heterocyclic group bonded via nitrogen.

Furthermore, $R_2$ of formulas I & Ia above also represents $NR_4R_5$, wherein $R_4$ represents:

(a) hydrogen;
(b) straight or branched chain lower alkyl;
(c) cycloalkyl;
(d) aryl;
(e) alkanoyl;
(f) benzoyl;
(g) amido;
(h) thioamido;
(i) amidino;
(j) benzyloxycarbonyl;
(k) trichloroethyloxycarbonyl;
(l) a heterocyclic group including heterocyclic alkyl wherein the heterocyclic group means a 5-(or 6-) membered ring containing from 1 to 4 of any one or more of the heteroatoms selected from O, S and N;
(m) heteroaroyl.

$R_5$ is hydrogen or any of the groups selected from (b) to (m) defined for $R_4$; and $R_4$ and $R_5$ may join together and form part of the heterocyclic group

which may contain one or more additional heteroatoms selected from N, S or O. The said heterocyclic ring may be unsubstituted or substituted with a substituent selected from the group consisting of methyl, carboxy, alkoxycarbonyl, hydroxy, hydroxymethyl.

Examples of such heterocyclic ring systems are:

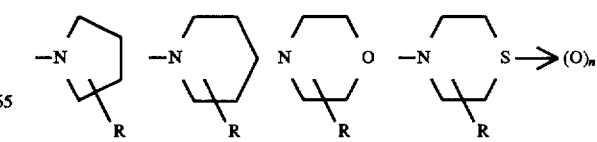

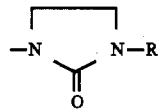

wherein R is hydrogen, lower alkyl, carboxy (including salt), alkoxycarbonyl, carboxymethyl (including salt), alkoxycarbonylmethyl. The terms "lower alkyl", "alkoxy" refer to groups having 1 to 4 carbon atoms.

$n=0, 1, 2$.

Preferred groups for $R_3$ are:

(a) hydrogen;
(b) straight or branched lower alkyl;
(c) lower alkenyl;
(d) lower alkynyl;
(e) cycloalkyl;
(f) cycloalkenyl;
(g) aryl;
(h) aralkyl;
(i) heteroaryl including the heteroaryl alkyl.

Even more preferably, $R_3$ group represents: hydrogen, methyl, ethyl, propyl, butyl, t-butyl, allyl, propargyl, isopropyl, cyclopentyl, cyclopropylmethyl, —CH$_2$COOC$_2$H$_5$, —CH$_2$COOH, —CH$_2$COOBu$^t$, hydroxyethyl, cyanomethyl, nitromethyl, aminoethyl, guanidinoethyl, amidinomethyl, amidinoethyl, bromoethyl, carboxamidomethyl, substituted carboxamidomethyl, methoxymethyl, benzyl, thienylmethyl, furylmethyl, 2-piperidinylmethyl, 2-(piperidin-1-yl)ethyl, pyridinylmethyl, azidoethyl, 1,2,3-triazol-1-yl ethyl, 2-methyl-1,3,4-thiadiazol-5-yl-thioethyl, 1-methyl-1,2,3,4-tetrazol-5-yl thioethyl, and the like.

Preferred groups at $R_4$ are:

(a) hydrogen;
(b) lower alkyl;
(c) aryl;
(d) acetyl;
(e) benzoyl;
(f) amido;
(g) thioamido;
(h) amidino;
i) benzyloxycarbonyl;
(j) trichloroethyloxycarbonyl;
(k) heteroaroyl, e.g. nicotinoyl.

$R_5$ has the same meaning as defined for $R_4$. $R_4$ and $R_5$ may join together to form part of the heterocyclic group

which may contain one or more additional heteroatoms selected from N, S or O. The said heterocyclic group may be substituted or unsubstituted.

Examples of such heterocyclic groups are:

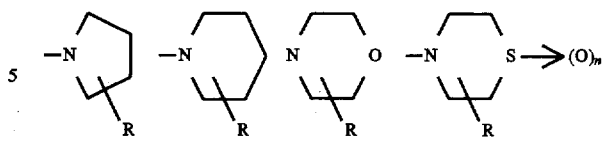

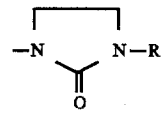

wherein R is hydrogen, lower alkyl, carboxy (including salt), alkoxycarbonyl, carboxymethyl (including salt), alkoxycarbonylmethyl. The terms "lower alkyl", "alkoxy" refer to groups having 1 to 4 carbon atoms.

$n=0, 1, 2$.

When $R_2$ in the formulas I & Ia represents OR$_3$, the OR$_3$ group may be in "syn" or "anti" configuration.

The penicillin derivatives of the present invention having the formulas I & Ia can be prepared by the processes shown in the equations below. The processes differ according to the kind of groups presented by $R_1$ and $R_2$.

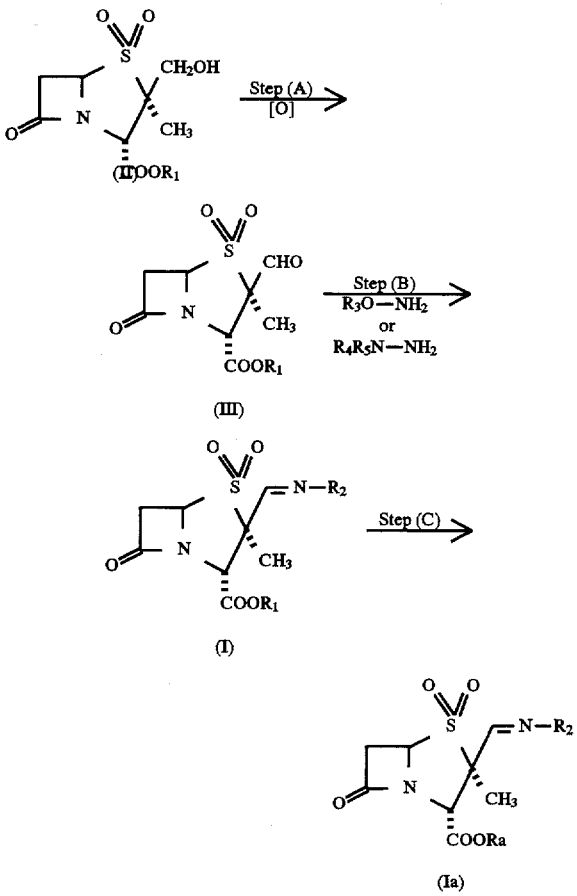

In the foregoing formulas, $R_1$, $R_2$ and $R_a$ are as defined before.

The 3-hydroxymethyl-3-methyl-4-thia-1-azabicyclo[3.2.0]heptane-2-carboxylate, 4,4-dioxide, the compound of formula (II), can be prepared by the method of D.O. Spry, J. Org. Chem., 44, 3084 (1979).

The steps (A), (B) and (C) of the foregoing process will be described below in detail.

STEP (A)

This is a classical oxidation reaction of a primary alcohol to an aldehyde and it can be brought about using a variety of reagents as described in "Comprehensive Organic Transformations" by Richard C. Larock, pp. 604–614 (published in 1989, VCH Publishers, Inc.). For example, one convenient oxidant is pyridinium chlorochromate. When a compound of formula (II) is oxidized to the corresponding compound of formula (III) using pyridinium chlorochromate, the reaction is usually carried out by treating the compound of formula (II) with from about 2 to about 6 molar equivalents, and preferably about 3 molar equivalents of the oxidant. The organic solvents useful in the reaction are not particularly limited and include any of those which do not adversely affect the reaction. Typical solvents are dichloromethane, chloroform, 1,2-dichloroethane, ethyl acetate, butyl acetate, and the like. The reaction is normally carried out at a temperature of from about −20° to about 50° C. and preferably from about 15° to about 30° C. After completion of the reaction, the desired product can be easily separated by conventional methods such as thin layer chromatography, column chromatography, crystallization or like methods.

STEP (B)

The compound (I), wherein $R_2$ is $OR_3$ can be prepared by reacting a compound (III) with a hydroxylamine derivative or its salt. The hydroxylamine derivative may be hydroxylamine substituted with one or more of the groups selected from methyl, ethyl, propyl, allyl, etc. Suitable salt of the hydroxylamine derivative may be hydrochloride, hydrobromide, sulfate or the like.

The reaction is usually conducted in a conventional solvent such as water, alcohol, tetrahydrofuran, acetonitrile, dimethylsulfoxide, pyridine or any other solvent which does not adversely influence the reaction, or a mixture thereof, and the reaction time is not critical.

In case that a salt of the hydroxylamine derivative is used as a reagent, the reaction is preferably conducted in the presence of a conventional base.

The compound (I), wherein $R_2$ is $NR_4R_5$, can be prepared by reacting a compound (III) with a hydrazine derivative or its salt. The hydrazine derivative may be hydrazine unsubstituted or substituted with acyl, benzoyl, amide, thioamide, benzyloxycarbonyl, nicotinoyl, or the like. A suitable salt of the hydrazine derivative may be hydrochloride, hydrobromide or the like.

This reaction may be conducted substantially in the same manner as the reaction of step (A).

STEP (C)

The compound of formula (I) is subjected to de-esterification without or after isolation from the reaction mixture obtained in step (B), whereby a penicillin derivative of the formula (Ia) in which $R_a$ is hydrogen is obtained.

As the de-esterification method, reduction, hydrolysis, treatment with an acid, phenol, m-cresol and the like can be employed for converting the carboxyl-protecting group to the carboxyl group. For example, if the carboxyl-protecting group is an active ester, the reaction frequently proceeds with ease under mild hydrolysis conditions or by bringing the ester into contact with water. The reduction method is employed when the carboxyl protecting group is trichloroethyl, benzyl, diphenylmethyl, p-nitrobenzyl or the like. Treatment with an acid is adopted when the carboxyl-protecting group is tert-butyl, diphenylmethyl, p-methoxybenzyl, trityl, methoxymethyl or the like. Treatment with tetrakis (triphenylphosphine)palladium(O) and triphenyl phosphine is adopted when the carboxyl-protecting group is allyl. If the carboxyl-protecting group is diphenyl methyl, it may be advantageous to remove the protecting group by heating with phenol, m-cresol, p-cresol or the like. Treatment with a Lewis acid aluminum chloride) in presence of a solvent (e.g. anisole, N,N-dimethylaniline) is also adopted when the carboxyl-protecting group is p-methoxybenzyl, benzyl or the like.

The reduction can be conducted by treating the ester of the formula (I), wherein $R_1$ is trichloroethyl, with a mixture of zinc, zinc-amalgam or the like metal and formic acid, acetic acid or like acid. Alternatively, the reduction can be conducted under an atmosphere of hydrogen, or hydrogen mixed with an inert diluent such as nitrogen or argon, in the presence of a hydrogenation catalyst. The catalysts used in this hydrogenation reaction are the type of agents known in the art for this kind of transformation and typical examples are the noble metals, such as nickel, palladium, platinum and rhodium. Examples of the catalysts are platinum, platinum oxide, palladium, palladium oxide, nickel oxide, Raney-nickel and the like. The catalyst is usually present in the amount from about 1 to about 20 weight-percent and preferably from about 5 to about 10 weight-percent, based on the compound of formula (I). It is often convenient to suspend the catalyst on an inert support. A particularly convenient catalyst is palladium suspended on an inert support such as carbon e.g. 10% by weight palladium on carbon.

Suitable solvents for this reaction are those which substantially dissolve the starting material of the formula (I), are sufficiently volatile to be removed by evaporation, and do not themselves suffer hydrogenation. Examples of such solvents include methanol, ethanol, dioxane, tetrahydrofuran, diethyl ether, 1,2-dimethoxyethane, ethyl acetate, butyl acetate, acetic acid, trifluoroacetic acid; and a mixture of these organic solvents and water.

The acids useful for eliminating the carboxyl-protecting group of the ester of the formula (I) are formic acid, trichloroacetic acid, trifluoroacetic acid, hydrochloric acid, hydrofluoric acid, p-toluene sulfonic acids, trifluoromethanesulfonic acid and the like. When the acid is used in a liquid state, it can act also as a solvent. Alternatively, an organic solvent can be used as a co-solvent. Useful solvents are not particularly limited as far as they do not adversely affect the reaction. Examples of useful solvents are anisole, trifluoroethanol, dichloromethane, dimethylformamide and like solvents.

The penicillin derivative of the present invention having the formula (Ia) in which $R_a$ is hydrogen can be purified by standard procedures in the art, such as recrystallization or chromatography, e.g. chromatography on sephadex.

The β-lactamase inhibitors of this invention of formula (Ia) are acidic, and they will form salts with basic agents. It is necessary to use a pharmaceutically acceptable non-toxic salt. Moreover, when $R_a$ is hydrogen, a compound of formula (Ia) is a mono-acid and will form a mono-salt. Alternatively, it can form an internal salt (zwitterion) by interaction with a basic nitrogen atom present in the molecule of formula (Ia). However, when $R_a$ is hydrogen and $R_2$ is $OR_3$, wherein the residue $R_3$ contains a carboxylic group, the compound of the formula (Ia) is a diacid and can form disalts. In the latter case, the two cationic counterions can be the same or different. Salts of the compounds of formula (Ia) can be prepared by standard methods known in the penicillin and cephalosporin literature. Typically, this involves contacting the acidic and basic components in the appropriate stoichiometric ratio in an inert solvent system which can be aqueous, non-aqueous or partially aqueous, as appropriate.

Favorable pharmaceutically-acceptable salts of the compounds of formula (Ia) are sodium, potassium, calcium and triethylamine salts.

In regard to esters readily hydrolyzable in vivo of a compound of the formula (Ia), it is necessary to use a pharmaceutically-acceptable non-toxic ester. Such esters are prepared by standard methods, with the specific method being chosen being dependent upon the precise ester to be prepared. If the ester residue is, for example, 3-phthalidyl, 4-crotonolactonyl, gamma-butyrolacton-4-yl or the like, the esters can be prepared by alkylation of a carboxylate salt of a compound of formula (Ia) with 3-halogenated phthalide, 4-halogenated crotonolactone, 4-halogenated-gamma-butyrolactone or the like. The reaction is carried out by dissolving the salt of the penicillin derivative of the formula (Ia) in a suitable polar organic solvent, such as N,N-dimethylformamide, and then adding about one molar equivalent of the halide. Suitable salts of the penicillin derivative to be used in the esterification are salts of sodium, potassium or like alkali metals; salts of triethylamine, ethyldiisopropylamine, N,N-dimethylaniline, N-ethylpiperidine, N-methylmorpholine or like tertiary amines. The reaction temperature ranges from about 0° to about 100° C., preferably from about 15° to about 25° C. The length of time needed to reach essentially completion varies according to a variety of factors, such as the concentration of the reactants and the reactivity of the reagents. Thus, when considering the halo compound, the iodide reacts faster than the bromide, which in turn reacts faster than the chloride.

After completion of the reaction, the desired product can be easily separated by conventional methods and purified, when required, by recrystallization, column chromatography or the like.

The compounds of the present invention, including the pharmaceutically-acceptable salts thereof, and the pharmaceutically-acceptable readily in vivo hydrolyzable esters thereof are inhibitors of bacterial β-lactamases. The compounds increase the antibacterial effectiveness of β-lactamase susceptible β-lactam antibiotic—that is, they increase the effectiveness of the antibiotic against infections caused by β-lactamase producing microorganisms in mammalian subjects. This makes the compounds of formula (Ia), and said pharmaceutically acceptable salts and esters thereof, valuable for co-administration with β-lactam antibiotics in the treatment of bacterial infections in mammalian subjects, particularly humans. In the treatment of a bacterial infection, said compound of the formula (Ia) or salt or ester thereof can be mixed with the beta-lactam antibiotic, and the two agents thereby administered simultaneously. Alternatively, the compound of formula (Ia) or salt or ester thereof can be administered as a separate agent during a course of treatment with the antibiotic.

A compound of formula (Ia) or salt or ester thereof can be administered orally or parenterally. The salts of the compounds of formula (Ia) tend to be more effective when administered parenterally, whereas in many instances formation of an ester readily hydrolyzable in vivo increases oral effectiveness. The compounds of the present invention can be administered alone, or may be mixed with a pharmaceutically-acceptable carrier or diluent depending on the mode of administration. For oral mode of administration, a compound of this invention can be used in the form of tablets, capsules, granules, powders, lozenges, troches, syrups, elixirs, solution, suspensions and the like, in accordance with the standard pharmaceutical practice.

For parenteral administration, which includes intramuscular, intraperitoneal, subcutaneous and intravenous use, sterile solutions of the active ingredient are usually prepared, and the pH of the solutions are suitably adjusted and buffered. For intravenous use, the total concentration of solutes should be controlled to render the preparation isotonic.

Carriers useful in formulating the preparations are commonly used pharmaceutically acceptable non-toxic carriers such as gelatin, lactose, sodium citrate, salts of phosphoric acid, starch, magnesium stearate, sodium lauryl sulphate, talc, polyethylene glycol etc. The carrier may be used with other additives such as diluents, binders, buffer agents, preservatives, sweetening agents, flavoring agents, glazes, disintegrators, coating agents, emulsifying agents, suspending agents, etc. In a pharmaceutical composition containing a compound of this invention, the weight ratio of active ingredient to carrier will normally be in the range from 1:20 to 20:1.

The daily dose of the preparation can be appropriately determined and is not particularly limited. However, in most instances, an effective β-lactamase inhibiting dose of a compound of formula (Ia), or pharmaceutically acceptable salt or ester thereof, will be a daily dose in the range from about 1 to about 500 mg per kilogram of body weight orally, and from about 1 to about 500 mg per kilogram of body weight parenterally. However, in some cases, it may be necessary to use dosages outside these ranges. The weight ratio of the compound of the present invention and the β-lactam antibiotic with which it is being administered will normally be in the range from 1:20 to 20:1.

The following examples are provided to demonstrate the operability of the present invention. The structures of the compounds were established by the modes of synthesis and by extensive high field nuclear magnetic resonance spectral techniques.

EXAMPLE 1

Preparation of diphenylmethyl (2S, 3R, 5R)-3-formyl-3-methyl-7-oxo-4-thia-1-azabicyclo[3.2.0]heptane-2-carboxylate, 4,4-dioxide (step A, compound 1)

To a stirred solution of diphenylmethyl (2S, 3S, 5R)-3-hydroxymethyl-3-methyl-7-oxo-4-thia-1-azabicyclo[3.2.0] heptane-2-carboxylate, 4,4-dioxide (6.84 gm, 16.46 mmol) in dry methylene chloride (340 ml), was added pyridinium chlorochromate (7.1 gm) in one portion. The mixture was stirred at room temperature for 18 h, an additional amount of pyridinium chlorochromate (1.78 gm) was added, and the mixture stirred for additional 5 h. The reaction mixture was diluted with methylene chloride, treated with charcoal and filtered through a bed of Celite. The filtrate was washed with water, brine, dried ($Na_2SO_4$) and evaporated to give a foam (5.14 gm, 76% yield).

$^1$H NMR (DMSO-$d_6$): δ9.85 (s, 1H); 7.23–7.38 (m, 10H); 6.85 (s, 1H); 5.82 (s, 1H); 5.25 (dd, 1H, $J_1$=1.2 Hz, $J_2$=4.43 Hz); 3.74 (dd, 1H, $J_1$=4.43 Hz, $J_2$=16.7 Hz); 3.30 (dd, 1H, $J_1$=1.2 Hz, $J_2$=16.7 Hz); 1.26 (s, 3H).

EXAMPLE 2

Preparation of diphenylmethyl (2S, 3R, 5R)-3-formyl-3-methyl-7-oxo-4-thia-1-azabicyclo[3.2.0]heptane-2-carboxylate, 3$^1$-(O-methyloxime), 4,4-dioxide (Step B, compound 2)

A suspension of compound 1 (1.0 gm, 2.42 mmol) in 95% ethanol (50 ml) was treated with methoxylamine hydrochloride (242 mg, 2.903 mmol) followed by pyridine (230 mg, 2.903 mmol) and the mixture was stirred at room temperature for 5 h and concentrated under reduced pressure. The residue was dissolved in methylene chloride, washed with 5% HCl, water and brine. After drying ($Na_2SO_4$), the solvent was removed under reduced pressure to give a foam (1.0 gm) which was purified over a silica gel column using hexane-ethyl acetate as eluant. The desired compound was obtained as a foam, 467 mg (44%).

$^1$H NMR (DMSO-$d_6$): δ7.89 (s, 1H); 7.22–7.40 (m, 10H); 6.86 (s, 1H); 5.39 (s, 1H); 5.26 (dd, 1H, $J_1$=1.4 Hz, $J_2$=4.4 Hz); 3.82 (s, 3H); 3.68 (dd, 1H, $J_1$=4.6 Hz, $J_2$=16.7 Hz); 3.26 (dd, 1H, $J_1$=1.4 Hz, $J_2$=16.7 Hz); 1.28 (s, 3H).

EXAMPLE 3 preparation of sodium (2S, 3R, 5R)-3-formyl-3-methyl-7-oxo-4-thia-1-azabicyclo[3.2.0]heptane-2-carboxylate, 3$^1$-(O-methyloxime), 4,4-dioxide (Step C, compound 3)

To a solution of compound 2 (294 mg, 0.664 mmol) in dry anisole (768 µl) at −5° C. under $N_2$, was added TFA (758 mg, 512 µl) and stirred at 0° C. for 3.5 h. The mixture was concentrated to dryness under reduced pressure and the residue was triturated with a mixture of ether-hexane. The precipitated solid was collected by filtration (186 mg). The solid thus obtained was treated with a solution of $NaHCO_3$ (113 mg) dissolved in water (10 ml), stirred at room temperature for 10 min and freeze dried to give a fluffy solid (229 mg) which was purified by reverse phase preparative tlc using acetonitrile-water (7:1.5) as the developing solvent. The desired salt was obtained as a fluffy solid (44 mg, 22%).

$^1$H NMR (DMSO-$d_6$): δ7.55 (s, 1H); 5.03 (br, d, 1H, J=2.9 Hz); 4.32 (s, 1H); 3.83 (s, 3H); 3.55 (dd, 1H, $J_1$=4.2 Hz, $J_2$=16.1 Hz); 3.12 (dd, 1H, $J_1$=1.3 Hz, $J_2$=16.1 Hz); 1.52 (s, 3H).

EXAMPLE 4

Preparation of diphenymethyl (2S, 3R, 5R)-3-formyl-3-methyl-7-oxo-4-thia-1-azabicyclo[3.2.0]heptane-2-carboxylate, 3$^1$-(hydroxyloxime), 4,4-dixoide (compound 4)

To a solution of compound 1 (2.5 gm, 6.05 mmol) in a mixture of methylene chloride (30 ml) and ethanol (60 ml) was added hydroxylamine hydrochloride (504 mg, 7.26 mmol) followed by pyridine (430 mg, 440 µl) and the mixture was stirred at room temp. for 5.5 h. The mixture was concentrated to dryness and the residue was dissolved in ethyl acetate, washed with brine, dried ($Na_2SO_4$) and concentrated to give a foam. Purification of the crude product over a silica gel column using benzene-ethyl acetate (10:1) gave the pure product (900 mg, 35% yield).

$^1$H NMR (DMSO-$d_6$): δ12.0 (s, 1H); 7.81 (s, 1H); 7.29–7.46 (m, 10H); 6.92 (s, 1H); 5.40 (s, 1H); 5.30 (br, d, J=2.9 Hz); 3.74 (dd, 1H, $J_1$=4.5 Hz, $J_2$=16.6 Hz); 3.32 (dd, 1H, $J_2$=1.2 Hz, $J_2$=16.6 Hz); 1.36 (s, 3H).

EXAMPLE 5

Preparation of sodium (2S, 3R, 5R)-3-formyl-3-methyl-7-oxo-4-thia-1-azabicyclo[3.2.0]heptane-2-carboxylate, 3$^1$-(hydroxyloxime), 4,4-dioxide (compound 5)

A mixture of compound 4 (200 mg, 0.47 mmol) in ethanol (20 ml) and 10% Pd/C (200 mg) was hydrogenated at 50 psi for 5.5 h. The reaction mixture was then filtered through a bed of Celite and the filtrate was concentrated under reduced pressure. The residue was triturated with a mixture of ether-hexane to give a white solid which was collected by filtration (68 mg). The acid thus obtained was dissolved in a solution of $NaHCO_3$ (24 mg) dissolved in water (10 ml), and the mixture was stirred at room temperature for 10 min, then freeze-dried to give a white solid (75 mg). The product was purified by reverse phase preparative tlc using acetonitrile-water (7:1.5) as developing solvent. The pure product was obtained as a white fluffy solid, 30 mg (23% yield).

$^1$H NMR (DMSO-$d_6$): δ11.56 (s, 1H); 7.42 (s, 1H); 5.00 (br, d, 1H, J=2.9 Hz); 4.27 (s, 1H); 3.54 (dd, 1H, $J_1$=4.6 Hz, $J_2$=16.6 Hz); 3.12 (dd, 1H, $J_1$=1.2 Hz, $J_2$=16.5 Hz); 1.53 (s, 3H).

EXAMPLE 6

Preparation of diphenylmethyl (2S, 3R, 5R)-3-formyl-3-methyl-7-oxo-4-thia-1-azabicyclo[3.2.0]heptane-2-carboxylate, 3$^1$-(O-allyloxime), 4,4-dioxide (compound 6)

To a stirred solution of compound 1 (2.23 gm, 5.39 mmol) in a mixture of methylene chloride (30 ml) and ethanol (60 ml), was added allyloxyamine hydrochloride (709 mg, 6.47 mmol) followed by pyridine (384 mg, 393 µl). The mixture was stirred at room temperature for 6 h and concentrated to dryness. The residue was partitioned between ethyl acetate and water. The ethyl acetate layer was separated out, washed with 10% HCl, water, brine, dried ($Na_2SO_4$) and concentrated to give a gummy mass (2.78 gm) which was purified over a silica gel column using benzene-ethyl acetate (30: 1) as eluant. The product was obtained as a foam (800 mg, 32% yield).

$^1$H NMR (DMSO-$d_6$): δ8.01 (s, 1H); 7.30–7.46 (m, 10H); 6.93 (s, 1H); 5.87–6.08 (m, 1H); 5.47 (s, 1H); 5.18–5.40 (m, 3H); 4.62 (d, 2H, J=5.6 Hz); 3.76 (dd, 1H, $J_1$=4.5 Hz, $J_2$=16.7 Hz); 3.34 (dd, 1H, $J_1$=1.5 Hz, $J_2$=16.7 Hz); 1.35 (s, 3H).

EXAMPLE 7

Preparation of sodium (2S, 3R, 5R)-3-formyl-3-methyl-7-oxo-4-thia-1-azabicyclo[3.2.0]heptane-2-carboxylate, 3$^1$-(O-allyloxime), 4,4-dioxide. (Compound 7)

A solution of compound 6 (300 mg, 0.64 mmol) in anisole (740 µl) at −5° C. was treated with TFA dropwise (493 µl) and the mixture was stirred at 0° C. for 3.5 h. Volatile materials were removed under reduced pressure and the residue was triturated with a mixture of hexane-ether. The precipitated yellow solid was collected by filtration (84 mg). The solid thus obtained was treated with $NaHCO_3$ (69 mg) dissolved in water (10 ml) and the mixture was stirred at room temperature for 15 min and freeze-dried to give a yellow solid (121 mg) which was purified by reverse phase preparative tlc to give a light yellow fluffy solid, 15 mg (7% yield).

$^1$H NMR (DMSO-$d_6$): δ7.59 (s, 1H); 5.90–6.05 (m, 1H); 5.20–5.40 (m, 2H); 5.02 (br, d, 1H, J=2.9 Hz); 4.58 (d, 2H, J=5.6 Hz); 4.32 (s, 1H); 3.54 (dd, 1H, $J_1$=4.1 Hz, $J_2$=16.0 Hz); 3.14 (dd, 1H, $J_1$=1.2 Hz, $J_2$=16.0 Hz); 1.52 (s, 3H).

EXAMPLE 8

Preparation of sodium (2S, 3R, 5R)-3-formyl-3-methyl-7-oxo-4-thia-1-azabicyclo[3.2.0]heptane-2-carboxylate, 3$^1$-(O-propyloxime), 4,4-dioxide (compound 8)

A suspension of compound 6 (170 mg, 0.368 mmol) in 98% ethanol (25 ml) was hydrogenated for 3 h over 10% Pd/C (170 mg). The reaction mixture was filtered through a bed of Celite and the filtrate was concentrated to give a residue which was triturated with hexane followed by ether-hexane mixture. The precipitated solid was collected by filtration (49 mg). The acid thus obtained was treated with a solution of $NaHCO_3$ (27 mg) dissolved in water (10 ml). To this solution, 3 ml of acetonitrile was added and was stirred at room temperature for 15 min, and freeze-dried to give a white fluffy solid (67 mg). The solid was purified by reverse phase preparative tlc ($CH_3CN$-water, 7:1) gave a white fluffy solid (31 mg. 26% yield).

$^1$H NMR (DMSO-$d_6$): δ7.52 (s, 1H); 5.00 (br, d, 1H, J=3.0 Hz); 4.30 (s, 1H); 4.00 (t, 2H, J=6.7 Hz); 3.55 (dd, 1H, $J_1$=4.3 Hz, $J_2$=16.0 Hz); 3.12 (dd, 1H, $J_1$=1.2 Hz, $J_2$=16.0 Hz); 1.56–1.80 (m, 2H); 1.52 (s, 3H); 0.89 (t, 3H, J=7.4 Hz).

EXAMPLE 9

Preparation of diphenylmethyl (2S, 3R, 5R)-3-formyl-3-methyl-7-oxo-4-thia-1-azabicyclo[3.2.0]heptane-2-carboxylate, $3^1$-(O-ethyloxime), 4,4-dioxide (compound 9)

To a solution of compound 1 (1.831 gm, 4.428 mmol) in a mixture of methylene chloride (24 ml) and ethanol (48 ml), were added ethyloxyamine hydrochloride (0.494 gm, 4.428 mmol) and pyridine (0.330 ml, 4.080 mmol). After stirring at room temperature for 6.5 h, the reaction mixture was evaporated to dryness and the residue was partitioned between water and ethyl acetate. The ethyl acetate layer was separated out, washed with 10% HCl, water, brine, dried ($Na_2SO_4$) and concentrated (1.99 gm). The crude product was purified on a silica gel column using benzene-ethyl acetate (30:1) to yield the pure compound (0.428 gm, 23%).

$^1$H NMR (DMSO-$d_6$): δ7.93 (s, 1H); 7.25–7.50 (m, 10H); 6.92 (s, 1H); 5.45 (s, 1H); 5.32 (dd, 1H, $J_1$=1.2 Hz, $J_2$=4.5 Hz); 4.13 (q, 2H, J=6.97 Hz); 3.75 (dd, 1H, $J_1$=4.5 Hz, $J_2$=16.6 Hz); 3.33 (dd, 1H, $J_1$=1.2 Hz, $J_2$=16.6 Hz); 1.36 (s, 3H); 1.21 (t, 3H, J=7.03 Hz).

EXAMPLE 10

Preparation of sodium (2S, 3R, 5R]-3-formyl-3-methyl-7-oxo-4-thia-1-azabicyclo[3.2.0]heptane-2-carboxylate, $3^1$-(O-ethyloxime), 4,4-dioxide (compound 10)

A suspension of compound 9 (0.298 gm, 0.653 mmol) in ethanol (35 ml) was hydrogenated over Pd/C (10%, 300 mg) at 50 psi for 2.5 h. The reaction mixture was filtered through a bed of Celite and the filtrate was evaporated to dryness. The residue was washed with hexane followed by ether. The precipitated solid was collected by filtration (0.143 gm, 75%). The acid thus obtained was dissolved in a solution of $NaHCO_3$ (0.0931 gm, 1.107 mmol) dissolved in water (10 ml); a few drops of acetonitrile was added to make the reaction mixture homogeneous. The reaction mixture was stirred at room temperature for 45 min and freeze-dried. Purification by reverse phase preparative tlc eluting with acetonitrile-water (7:1) yielded the pure product (0.089 gm, 59%) as a fluffy yellow solid.

$^1$H NMR (DMSO-$d_6$): δ7.53 (s, 1H); 5.02 (br, s, 1H); 4.34 (s, 1H); 4.09 (q, 2H, J=7.04 Hz); 3.56 (dd, 1H, $J_1$=4.3 Hz, $J_2$=16.1 Hz); 3.13 (dd, 1H, $J_1$=1.1 Hz, $J_2$=16.0 Hz); 1.53 (s, 3H); 1.20 (t, 3H, J=7.04 Hz).

EXAMPLE 11

Preparation of diphenylmethyl (2S, 3R, 5R)-3-formyl-3-methyl-7-oxo-4-thia-1-azabicyclo[3.2.0]heptane-2-carboxylate, $3^1$-[O-(2-hydroxyethyl)oxime], 4,4-dioxide (compound 11)

To a solution of compound 1 (1.5 gm, 3.519 mmol) in a mixture of methylene chloride (20 ml) and ethanol (98%, 40 ml), were added 2-hydroxyethyloxyamine hydrochloride (0.955 gm, 3.519 mmol) and pyridine (0.260 ml, 3.215 mmol), and the reaction mixture was stirred for 6 h. The solvent was removed under reduced pressure and the residue was partitioned between water and ethyl acetate. The ethyl acetate layer was separated out, washed with 10% HCl, water, brine, dried ($Na_2SO_4$) and concentrated (1.83 gm). Purification by column chromatography over a silica gel column using benzene-ethyl acetate (3:1) as eluant gave the pure product as a yellow oil, 0.202 gm (12%).

$^1$H NMR (DMSO-$d_6$): δ7.95 (s, 1H); 7.29–7.45 (m, 10H); 6.93 (s, 1H); 5.46 (s, 1H); 5.31 (br, d, 1H, J=2.5 Hz); 4.80 (t, 1H, J=5.4 Hz); 4.12 (t, 2H, J=5.0 Hz); 3.75 (dd, 1H, $J_1$=4.2 Hz, $J_2$=16.0 Hz); 3.60–3.72 (m, 2H); 3.35 (dd, 1H, $J_1$=1.2 Hz, $J_2$=16.0 Hz); 1.34 (s, 3H).

EXAMPLE 12

Preparation of sodium (2S, 3R, 5R)-3-formyl-3-methyl-7-oxo-4-thia-1-azabicyclo[3.2.0]heptane-2-carboxylate, $3^1$-[O-(2-hydroxyethyl) oxime], 4,4-dioxide (compound 12)

A mixture of compound 11 (0.188 gm, 0.398 mmol) and Pd/C (10%, 0.190 gm) in ethanol (10 ml) was hydrogenated at 50 psi for 2.5 h, filtered through a bed of Celite, and the filtrate was evaporated to give a white solid (0.115 gm). The solid thus obtained was suspended in 10 ml of water. A few drops of acetonitrile was added followed by $NaHCO_3$ (0.063 gm, 7.437 mmol) and stirred for 0.5 h at room temp. After freeze drying, the product was purified by reverse phase preparative tlc (acetonitrile-water, 5:1) to yield 0.084 gm of a pale yellow solid in 58% yield.

$^1$H NMR (DMSO-$d_6$): δ7.55 (s, 1H); 5.03 (br, d, 1H, J=2.5 Hz); 4.78 (br, s, 1H); 4.34 (s, 1H); 4.07 (t, 2H, J=4.9 Hz); 3.50–3.68 (m, 3H); 3.10 and 3.18 (2s, 1H); 1.53 (s, 3H).

EXAMPLE 13

Preparation of diphenylmethyl (2S, 3R, 5R)-3-formyl-3-methyl-7-oxo-4-thia-1-azabicyclo[3.2.0]heptane-2-carboxylate, $3^1$-[O-[(2-pyridinium-1-yl) ethyl]oxime], 4,4-dioxide, trifluoromethane sulfonate salt. (compound 13)

To a stirred solution of compound 11 (417 mg, 0.882 mmol) in dry methylene chloride (10 ml) at −40° C., were added trifluoromethanesulfonic anhydride (520 µl) and pyridine (1.42 ml). The mixture was stirred at −40° C. for 3 h and at 0° C. for 1 h. Volatile materials were removed under reduced pressure and the residue was dissolved in chloroform (60 ml), washed with 10% aq. citric acid (50 ml), brine, dried ($Na_2SO_4$) and concentrated to give the desired product as an orange foam, 555 mg (92%).

$^1$H NMR (CDCl$_3$): δ8.91 (d, 2H, J=5.5 Hz); 8.40 (t, 1H, J=7.8 Hz); 7.98 (t, 2H, J=7.0 Hz); 7.20–7.42 (m, 10H); 6.93 (s, 1H); 5.08 (s, 1H); 4.99–5.08 (m, 1H); 4.15–4.40 (m, 1H); 3.60 (dd, 1H $J_1$=4.5 Hz, $J_2$=16.6 Hz); 3.42 (dd, 1H, $J_1$=1.6 Hz, $J_2$=16.6 Hz); 1.29 (s, 3H).

EXAMPLE 14

Preparation of 2-carboxy (2S, 3R, 5R)-3-formyl-3-methyl-7-oxo-4-thia-1-azabicyclo[3.2.0]heptane, $3^1$-[O-[(2-pyridinium-1-yl)ethyl]oxime], 4,4-dioxide, inner salt (compound 14)

To a solution of compound 13 (250 mg, 0.37 mmol) in anisole (420 µl) at 0° C., TFA (422 µl, 5.48 mmol) was added and stirred at 0° C. for 2.5 h. Ether (6 ml) was added to the mixture and the precipitated solid was collected by filtration. The solid thus obtained was dissolved in a solution of $NaHCO_3$ (60 mg) dissolved in 10 ml of water and freeze-dried. The product was purified by reverse phase preparative tlc (acetonitrile-water), 11 mg (8%).

$^1$H NMR (D20): δ8.83 (d, 2H, J=5.7 Hz); 8.55 (t, 1H, J=5.7 Hz); 8.06 (t, 2H, J=5.7 Hz); 7.65 (s, 1H); 5.05 (dd, 1H, $J_1$=1.6 Hz, $J_2$=4.0 Hz); 4.95 (m, 2H); 4.82 (m, 2H); 4.64 (s, 1H); 3.68 (dd, 1H, $J_1$=4.3 Hz, $J_2$=16.8 Hz); 3.40 (dd, 1H, $J_1$=1.5 Hz, $J_2$=16.8 Hz); 1.25 (s, 3H).

EXAMPLE 15

Preparation of sodium (2S, 3R, 5R)-3-formyl-3-methyl-7-oxo-4-thia-1-azabicyclo[3.2.0]heptane-2-carboxylate, $3^1$-[O-[(2-piperidin-1-yl) ethyl]oxime], 4,4-dioxide (compound 15)

A suspension of compound 13 (300 mg, 0.438 mmol) in ethanol (15 ml) was hydrogenated over Pd/C (10%, 300 mg) at 50 psi for 18 h. The mixture was filtered through a bed of Celite and the filtrate was evaporated to dryness. The residue was dissolved in a solution of NaHCO₃ (50 mg) dissolved in 10 ml of water and a few drops of acetonitrile was added to make the mixture completely homogeneous. After freeze-drying the product was purified by preparative tlc (acetonitrile-water), 45% yield. $^1$H NMR (D₂O): δ7.74 (s, 1H); 5.10 (dd, 1H, $J_1$=1.6 Hz, $J_2$=4.0 Hz); 4.78 (s, 1H); 4.50 (t, 2H, J=5.0 Hz); 3.70 (dd, 1H, $J_1$=4.3 Hz, $J_2$=16.7 Hz); 3.43 (dd, 1H, $J_1$=1.6 Hz, $J_2$=16.7 Hz); 3.15–3.45 (m, 6H); 1.70–1.86 (m, 4H); 1.50–1.70 (m, overlapped with a singlet, 5H).

EXAMPLE 16

Preparation of diphenylmethyl (2S, 3R, 5R)-3-formyl-3-methyl-7-oxo-4-thia-1-azabicyclo[3.2.0]heptane-2-carboxylate, $3^1$-[O-(methoxymethyl)oxime], 4,4-dioxide (compound 16)

This compound was prepared in the same manner as described for compound 2; methoxymethyloxyamine hydrochloride was used in place of methoxylamine hydrochloride. The product was obtained in 33% yield.

$^1$H NMR (CDCl₃): δ7.64 (s, 1H); 7.28–7.40 (m, 10H); 6.93 (s, 1H); 5.17 (q, 2H, J=7.3 Hz); 5.09 (s, 1H); 4.64 (br, t, 1H); 3.50 (t, 2H); 3.40 (s, 3H); 1.34 (s, 3H).

EXAMPLE 17

Preparation of sodium (2S, 3R, 5R)-3-formyl-3-methyl-7-oxo-4-thia-1-azabicyclo[3.2.0]heptane-2-carboxylate, $3^1$-[O-(methoxymethyl)oxime], 4,4-dioxide (compound 17)

A solution of compound 16 (370 mg, 0.783 mmol) in ethanol (20 ml) was hydrogenated over Pd/C (10%, 370 mg) at 50 psi for 5 h. The reaction mixture was filtered through Celite, the filtrate was concentrated under reduced pressure and the residue was treated with a solution of NaHCO₃ (70 m₉) dissolved in 10 ml of water. After freeze-drying and purification by reverse phase preparative tlc, the product was obtained in 70% yield (180 mg).

$^1$H NMR (D20): δ7.81 (s, 1H); 5.17 (s, 2H); 5.09 (dd, 1H, $J_1$=1.6 Hz, $J_2$=4.2 Hz); 4.78 (s, 1H); 3.68 (dd, 1H, $J_1$=4.3 Hz, $J_2$=16.8 Hz); 3.40 (dd, 1H, $J_1$=1.6 Hz, $J_2$=16.8 Hz); 3.48 (s, 3H); 1.65 (s, 3H).

EXAMPLE 18

Preparation of diphenylmethyl (2S, 3R, 5R)-3-formyl-3-methyl-7-oxo-4-thia-1-azabicyclo[3.2.0]heptane-2-carboxylate, $3^1$-(O-t-butyloxime), 4,4-dioxide (compound 18)

A solution of compound 1 (1.81 gm, 4.39 mmol) in a mixture of ethanol (98%, 20 ml) and methylene chloride (15 ml) was treated with 0.5 gm (3.98 mmol) of t-butoxylamine hydrochloride followed by triethylamine (0.282 gm, 2.79 mmol) and the mixture was stirred at room temperature overnight. Solvent was removed under reduced pressure and the residue was dissolved in methylene chloride, washed with water, brine, dried (Na₂SO₄) and concentrated under reduced pressure. Purification by silica gel column chromatography using hexane-ethyl acetate (3:2) gave the desired product, 350 mg (16.5%).

$^1$H NMR (DMSO-d₆): δ7.82 (s, 1H); 7.29–7.43 (m, 10H); 6.92 (s, 1H; 5.44 (s, 1H); 5.30 (dd, 1H, $J_1$=1.2 Hz, $J_2$=4.5 Hz); 3.74 (dd, 1H, $J_1$=4.5 Hz, $J_2$=16.6 Hz); 3.30 (dd, 1H, $J_1$=1.2 Hz, $J_2$=16.6 Hz); 1.38 (s, 3H); 1.24 (s, 9H).

EXAMPLE 19

Preparation of sodium (2S, 3R, 5R)-3-formyl-3-methyl-7-oxo-4-thia-1-azabicyclo[3.2.0]heptane-2-carboxylate, $3^1$-(O-t-butyloxime), 4,4-dioxide (compound 19)

A solution of compound 18 (315 mg, 0.65 mmol) in a mixture of ethyl acetate (6 ml) and ethanol (20 ml) was hydrogenated over Pd/C (10%, 310 mg) at 50 psi for 8 h, filtered through a bed of Celite, and concentrated under reduced pressure. The residue was dissolved with ether, and the solid thus obtained was suspended in water (10 ml). NaHCO₃ (55 mg) was added and stirred at room temperature for 30 min, then freeze-dried. The crude product (200 mg) was purified by reverse phase preparative tlc (acetonitrile-water, 8:1) to yield the pure compound (66 mg).

$^1$H NMR (DMSO-d₆): δ7.44 (s, 1H); 4.98 (dd, 1H, $J_1$=1.1 Hz, $J_2$=4.0 Hz); 4.33 (s, 1H); 3.53 (dd, 1H, $J_1$=4.3 Hz, $J_2$=16.0 Hz); 3.12 (dd, 1H, $J_1$=1.1 Hz, $J_2$=16.0 Hz); 1.54 (s, 3H); 1.25 (s, 9H).

EXAMPLE 20

Preparation of diphenylmethyl (2S, 3R, 5R)-3-formyl-3-methyl-7-oxo-4-thia-1-azabicyclo[3.2.0]heptane-2-carboxylate, $3^1$-[O-(carboxamidomethyl)oxime], 4,4-dioxide (compound 20)

A solution of compound 1 (2.55 gm, 6.163 mmol) in methylene chloride (20 ml) and ethanol (25 ml) was treated with carboxamidomethyloxy amine hydrochloride (0.65 gm, 5.136 mmol) followed by pyridine (0.284 gm) and the mixture was stirred at room temperature for 10 h. Solvent was removed under reduced pressure and the residue was dissolved in methylene chloride, washed with water, brine, dried (Na₂SO₄) and evaporated in vacuo to give a gummy mass which was purified by silica gel column chromatography using hexane-ethyl acetate (1:1) as eluant. The pure compound was obtained in 16% yield (0.472 gm).

$^1$H NMR (DMSO-d₆): δ8.05 (s, 1H); 7.29–7.47 (m, 12H); 6.93 (s, 1H); 5.44 (s, 1H); 5.32 (d, 1H, J=3.0 Hz); 4.49 (s, 2H); 3.76 (dd, 1H, $J_1$=3.5 Hz, $J_2$=16.0 Hz); 3.34 (dd, 1H, $J_1$=1.1 Hz, $J_2$=16.0 Hz); 1.32 (s, 3H).

EXAMPLE 21

Preparation of sodium (2S, 3R, 5R)-3-formyl-3-methyl-7-oxo-4-thia-1-azabicyclo[3.2.0]heptane-2-carboxylate, $3^1$-[O-(Carboxamidomethyl)oxime], 4,4-dioxide (compound 21)

A mixture of compound 20 (380 mg, 0.783 mmol) and Pd/C (10%, 380 mg) in ethyl acetate (5 ml) and ethanol (15 ml) was hydrogenated at 50 psi for 8 h. After filtration through a bed of Celite, the filtrate was concentrated under reduced pressure. The residue was triturated with ether to give a white solid which was suspended in water (10 ml) and NaHCO$_3$ (66 mg) was added. The mixture was stirred at room temperature for 30 min and then freeze-dried. The product was purified by reverse phase preparative tlc (acetonitrile-water, 7:3).

$^1$H NMR (DMSO-d$_6$): δ7.69 (s, 1H); 7.28 (d, 2H, J=19.6 Hz); 5.03 (br, d, 1H); 4.43 (s, 2H); 4.31 (s, 1H); 3.55 (dd, 1H, J$_1$=4.0 Hz, J$_2$=16.0 Hz); 3.14 (dd, 1H, J$_1$=1.0 Hz, J$_2$=16.0 Hz); 1.51 (s, 3H).

EXAMPLE 22

Preparation of diphenylmethyl (2S, 3R, 5R)-3-formyl-3-methyl-7-oxo-4-thia-1-azabicyclo[3.2.0]heptane-2-carboxylate, 3$^1$-(O-cyclopentyloxime), 4,4-dioxide (compound 22)

To a solution of compound 1 (1.0 gm, 2.42 mmol) in a mixture of methylene chloride (15 ml) and ethanol (15 ml), was added cyclopentyloxyamine hydrochloride (0.277 gm, 2.013 mmol) followed by pyridine (0.127 gm). The mixture was stirred for 20 h at room temperature. After usual work up and purification as described before, the desired compound was obtained (56 mg).

$^1$H NMR (DMSO-d$_6$): δ7.86 (s, 1H); 7.34–7.40 (m, 10H); 6.93 (s, 1H); 5.43 (s, 1H); 5.31 (br, d, 1H, J=3.0 Hz); 4.70 (m, 1H); 3.70 (dd, 1H, J$_1$=4.5 Hz, J$_2$=16.1 Hz); 3.30 (dd, 1H, J$_1$=1.1 Hz, J$_2$=16.0 Hz); 1.50–1.80 (m, 8H); 1.36 (s, 3H).

EXAMPLE 23

Preparation of diphenylmethyl (2S, 3R, 5R)-3-formyl-3-methyl-7-oxo-4-thia-1-azabicyclo[3.2.0]heptane-2-carboxylate, 3$^1$-(O-propargyloxyamine), 4,4-dioxide (compound 23)

A mixture of the aldehyde (compound 1, 1.62 gm, 3.91 mmol), propargyloxyamine hydrochloride (0.35 gm, 3.26 mmol), pyridine (0.206 gm) in methylene chloride (10 ml) and ethanol (15 ml), was stirred at room temp. for 20 h. After usual workup and purification as described before, the desired compound was obtained in 19% yield (360 mg).

$^1$H NMR (DMSO-d$_6$): δ8.05 (s, 1H); 7.25–7.46 (m, 10H); 6.92 (s, 1H); 5.48 (s, 1H); 5.33 (br, d, 1H, J=2.8 Hz); 4.77 (d, 2H, J=2.4 Hz); 3.75 (dd, 1H, J$_1$=4.5 Hz, J$_2$=16.2 Hz); 3.57 (br, t, 1H, J=2.3 Hz); 3.35 (dd, 1H, J$_1$=1.2 Hz, J$_2$=16.1 Hz); 1.34 (s, 3H).

EXAMPLE 24

Preparation of diphenylmethyl (2S, 3R, 5R)-3-formyl-3-methyl-7-oxo-4-thia-1-azabicyclo[3.2.0]heptane-2-carboxylate, 3$^1$-(O-benzyloxime), 4,4-dioxide (compound 24)

A mixture of the aldehyde (compound 1, 3.57 gm, 8.63 mmol), benzyloxyamine (0.673 gm, 6.17 mmol) in methylene chloride (25 ml) and ethanol (25 ml), and two drops of 6(N) HCl was stirred at room temperature for 20 h. After usual workup and column purification over a silica gel column (hexane-ethyl acetate) the desired compound was obtained as a white foam (1.27 gm).

$^1$H NMR (DMSO-d$_6$): δ8.04 (s, 1H); 7.28–7.52 (m, 15 H); 6.91 (s, 1H); 5.47 (s, 1H); 5.32 (br, d, 1H, J=3.0 Hz); 5.16 (br, s, 2H); 3.75 (dd, 1H, J$_1$=4.5 Hz, J$_2$=16.0 Hz); 3.32 (dd, 1H, J$_1$=1.1 Hz, J$_2$=16.0 Hz); 1.33 (s, 3H).

EXAMPLE 25

Preparation of diphenylmethyl (2S, 3R, 5R)-3-formyl-3-methyl-7-oxo-4-thia-1-azabicyclo[3.2.0]heptane-2-carboxylate, 3$^1$-[O-(cyclopropylmethyl) oxime], 4,4-dioxide (compound 25)

A mixture of the aldehyde (compound 1, 2.17 gm, 5.24 mmol), cyclopropylmethyloxyamine hydrochloride (0.54 gm, 4.37 mmol ), pyridine (283 µl) in methylene chloride (15 ml), and ethanol (20 ml) was stirred at room temperature for 20 h. After usual workup and column purification (hexane-ethyl acetate, 3:2) the product was obtained in 23% yield (590

$^1$H NMR (DMSO-d$_6$): δ7.93 (s, 1H); 7.25–7.50 (m, 10H); 6.92 (s, 1H); 5.43 (s, 1H); 5.32 (dd, 1H, J$_1$=1.5 Hz, J$_2$=3.0 Hz); 3.92 (d, 2H, J=7.1 Hz); 3.75 (dd, 1H, J$_1$=4.5 Hz, J$_2$=16.6 Hz); 3.33 (dd, 1H, J$_1$=1.2 Hz, J$_2$=16.6 Hz); 1.36 (s, 3H); 1.00–1.20 (m, 1H); 0.44–0.55 (m, 2H); 0.23–0.30 (m, 2H).

EXAMPLE 26

Preparation of sodium (2S, 3R, 5R)-3-formyl-3-methyl-7-oxo-4-thia-1-azabicyclo[3.2.0]heptane-2-carboxylate, 3$^1$-[O-(cyclopropylmethyl)oxime], 4,4-dioxide (compound 26)

A solution of compound 25 (350 mg, 0.73 mmol) in ethyl acetate (6 ml) and ethanol (15 ml) was hydrogenated over Pd/C (10%, 450 mg) at 50 psi for 8 h. The mixture was filtered through a bed of Celite and the filtrate was concentrated to dryness. The residue was digested with ether followed by hexane. The precipitated solid was collected by filtration and dissolved in a solution of NaHCO$_3$ (61 mg) dissolved in 10 ml of water and freeze-dried. The product was purified by reverse phase preparative tlc (acetonitrile-water, 7:3) to yield the pure compound, 54 mg (21% yield).

$^1$H NMR (DMSO-d$_6$): δ7.54 (s, 1H); 5.01 (br, d, 1H, J=3.0 Hz); 4.30 (s, 1H); 3.90 (d, 2H, J=7.2 Hz); 3.53 (dd, 1H, J$_1$=4.2 Hz, J$_2$=16.2 Hz); 3.13 (dd, 1H, J$_1$=1.1 Hz, J$_2$=16.1 Hz); 1.52 (s, 3H); 1.03–1.20 (m, 1H); 0.47–0.57 (m, 2H); 0.22–0.30 (m, 2H).

EXAMPLE 27

Preparation of diphenylmethyl (2S, 3R, 5R)-3-formyl-3-methyl-7-oxo-4-thia-1-azabicyclo[3.2.0]heptane-2-carboxylate, 3$^1$-[O-(diphenylmethyloxycarbonylmethyl) oxime], 4,4-dioxide (compound 27)

To a solution of the aldehyde (compound 1, 1.2 gm, 2.90 mmol) in a mixture of ethanol (15 ml) and methylene chloride (15 ml), was added diphenylmlmethyloxyamine (2.90 mmol, generated in situ from diphenylmethyloxycarbonylmethyloxy phthalimido by treatment with hydrazine), followed by 2 drops of conc.HCl and the mixture was stirred at room temp. for 14 h. After usual work up and column purification (hexane-ethyl acetate, 3:2), the product was obtained in 34% yield (645 mg).

$^1$H NMR (DMSO-d$_6$): δ8.10 (s, 1H); 7.12–7.42 (m, 20H); 6.82 and 6.85 (2s, 2H); 5.46 (s, 1H); 5.30 (br, d, 1H); 4.83 (ABq, 2H, J=16.0 Hz); 3.69 (dd, 1H, J$_1$=3.0 Hz, J$_2$=16.0 Hz); 3.25 (dd, 1H, J$_1$=1.0 Hz, J$_2$=16.0 Hz); 1.25 (s, 3H).

EXAMPLE 28

Preparation of (2S, 3R, 5R)-3-formyl-3-methyl-7-oxo-4-thia-1-azabicyclo[3.2.0]heptane-2-carboxylic acid, 3$^1$-[O-(carboxymethyl)oxime], disodium salt, 4,4-dioxide (compound 28)

A solution of compound 27 (480 mg, 0.74 mmol) in a mixture of ethanol (15 ml) and ethyl acetate (15 ml) was hydrogenated over 10% Pd/C (500 mg) for 8 h at 50 p.s.i. The catalyst was removed by filtration through Celite and the filtrate was evaporated under reduced pressure. The residue was triturated with a mixture of ethyl acetate-ether (1:1) to give a solid which was collected by filtration and air dried. The acid thus obtained was suspended in water (8 ml). NaHCO$_3$ (124 mg, 1.47 mmol) was added and stirred at room temperature for 1 h. After freeze-drying, the product was purified by reverse-phase preparative tlc using acetonitrile-water (7:1.5 as developing solvent (33 mg).

$^1$H NMR (D$_2$O): δ7.80 (s, 1H); 5.13 (dd, 1H, J$_1$=1.8 Hz, J$_2$=2.5 Hz); 4.82 (s, 1H); 4.59 (s, 2H); 3.73 (dd, 1H, J$_1$=4.3 Hz, J$_2$=16.8 Hz); 3.48 (dd, 1H, J$_1$=1.8 Hz, J$_2$=16.8 Hz); 1.68 (s, 3H).

EXAMPLE 29

Preparation of diphenylmethyl (2S, 3R, 5R)-3-formyl-3-methyl-7-oxo-4-thia-1-azabicyclo[3.2.0]heptane2-carboxylate, 3$^1$-[O-(t-butyloxycarbonylmethyl)oxime], 4,4-dioxide (compound 29)

To a solution of the aldehyde (compound 1, 326 mg, 0.79 mmol) in a mixture of ethanol (10 ml) and methylene chloride (5 ml), was added t-butyloxycarbonylmethyloxyamine (116 mg, 0.79 mmol) followed by one drop of 6 (N) HCl. The reaction mixture was stirred at room temperature for 21 h. Solvent was removed under reduced pressure and the residue was dissolved in methylene chloride, washed with water, brine, dried (Na$_2$SO$_4$) and evaporated. The crude product was purified by silica gel column chromatography using hexane-ethyl acetate (3:2) as eluant. The pure product was obtained in 30.6% yield (131 mg).

$^1$H NMR (DMSO-d$_6$): δ8.08 (s, 1H); 7.29–7.48 (m, 10H); 6.92 (s, 1H); 5.48 (s, 1H); 5.33 (br, d, 1H, J=3.0 Hz); 4.60 (ABq, 2H, J=12.0 Hz); 3.75 (dd, 1H, J$_1$=3.0 Hz, J$_2$=16.0 Hz); 3.34 (dd, 1H, J$_1$=1.1 Hz, J$_2$=16.0 Hz); 1.42 (s, 9H); 1.31 (s, 3H).

EXAMPLE 30

Preparation of sodium (2S, 3R, 5R)-3-formyl-3-methyl-7-oxo-4-thia-1-azabicyclo[3.2.0]heptane-2-carboxylate, 3$^1$-[O-(t-butyloxycarbonylmethyl)oxime], 4,4-dioxide (compound 30)

A solution of compound 29 (317 mg) in ethanol (20 ml) was hydrogenated over 10% Pd/C (300 mg) at 50 psi for 16 h; the catalyst was removed by filtration and the filtrate was concentrated under reduced pressure. The residue was triturated with a mixture of ether-hexane (1:1). The precipitated solid was collected by filtration (118 mg). The acid thus obtained was suspended in 4 ml of water. 26 mg of NaHCO$_3$ was added and stirred at room temp. for 30 min. After freeze-drying, the product was purified by reverse phase preparative tlc using acetonitrile-water (8:1) to give the pure compound in 36% yield (45 mg).

$^1$H NMR (DMSO-d$_6$): δ7.66 (s, 1H); 5.02 (br, d, 1H, J=2.9 Hz); 4.55 (br, d, 2H); 4.34 (s, 1H); 3.55 (dd, 1H, J$_1$=4.1 Hz, J$_2$=16.0 Hz); 3.15 (dd, 1H, J$_1$=1.0 Hz, J$_2$=16.0 Hz); 1.51 (s, 3H); 1.43 (s, 9H).

EXAMPLE 31

Preparation of (2S, 3R, 5R)-3-formyl-3-methyl-7-oxo-4-thia-1-azabicyclo[3.2.0]heptane-2-carboxylic acid, 3$^1$-[O-(1-carboxy-1-methylethyl)oxime], disodium salt, 4,4-dioxide (compound 31)

This compound was prepared in the same manner as described for compound 28.

$^1$H NMR (D$_2$O): 7.65 (s, 1H); 5.10 (br, d, 1H, J=3.0 Hz); 4.80 (s, 1H); 3.71 (dd, 1H, J$_1$=4.3 Hz, J$_2$=16.7 Hz); 3.45 (dd, 1H, J$_1$=1.0 Hz, J$_2$=16.5 Hz); 1.66 (s, 3H); 1.47 (s, 6H).

EXAMPLE 32

Preparation of diphenylmethyl (2S, 3R, 5R)-3-formyl-3-methyl-7-oxo-4-thia-1-azabicyclo[3.2.0]heptane-2-carboxylate, 3$^1$-[O-[2-(1H-1,2,3-triazol-1-yl)ethyl]oxime], 4,4-dioxide (compound 32)

To a stirred solution of the penam aldehyde (compound 1, 3.3 gm, 0.008 mmol) in a mixture of ethanol (20 ml) and methylene chloride (20 ml), was added 1,2,3-triazol-1-ylethyloxyamine hydrochloride (0.87 gm, 0.008 mmol) followed by pyridine (0.5 gm) and the mixture was stirred at room temp. overnight. After usual work up and column purification (hexane-ethyl acetate), the pure compound was obtained as a foam (900 mg).

$^1$H NMR (DMSO-d$_6$): δ7.98 and 8.00 (2s, 2H); 7.70 (s, 1H); 7.33–7.40 (m, 10H); 6.92 (s, 1H); 5.46 (s, 1H); 5.33 (br, d, 1H, J=3.0 Hz); 4.65 (br, d, 2H); 4.47 (br, t, 2H); 3.75 (dd, 1H, J$_1$=4.0 Hz, J$_2$=15.1 Hz); 3.32 (dd, 1H, J$_1$=1.0 Hz, J$_2$=15.0 Hz); 1.33 (s, 3H).

EXAMPLE 33

Preparation of sodium (2S, 3R, 5R)-3-formyl-3-methyl-7-oxo-4-thia-1-azabicyclo[3.2.0]heptane-2-carboxylate, 3$^1$-[O-(2-(1H-1,2,3-triazol-1-yl)ethyl)oxime], 4,4-dioxide (compound 33)

To a solution of compound 32 (400 mg) in ethanol (20 ml), was added 10% Pd/C (420 mg). The mixture was hydrogenated at 50 psi for 5 h. Solvent was removed under reduced pressure and the residue was digested with hexane. The precipitated solid was collected by filtration and air-dried. The acid thus obtained was suspended in 15 ml of water. NaHCO$_3$ was added and stirred at room temperature for 0.5 h. After purification by reverse phase preparative tlc (acetonitrile:water, 7: 1) and freeze-drying, the product was obtained as a fluffy mass (170 mg).

$^1$H NMR (DMSO-d$_6$); δ5 8.16 (s, 1H); 7.70 (s, 1H); 7.58 (s, 1H); 5.05 (br, d, 1H); 4.60–4.72 (m, 2H); 4.38–4.49 (m, 2H); 4.35 (s, 1H); 3.54 (dd, 1H, J$_1$=3.0 Hz, J$_2$=16.0 Hz); 3.14 (dd, 1H, J$_1$=0.9 Hz, J$_2$=16.0 Hz); 1.55 (s, 3H).

EXAMPLE 34

Preparation of diphenylmethyl (2S, 3R, 5R)-3-formyl-3-methyl-7-oxo-4-thia-1-azabicyclo[3.2.0]heptane-2-carboxylate, 3-[O-[(pyridin-2-yl) methyl]oxime], 4,4-dioxide (compound 34)

To a stirred solution of the penam aldehyde (compound 1, 3.5 gm) in a mixture of ethanol (20 ml) and methylene chloride (20 ml), was added pyridin-2 -yl methyloxyamine hydrochloride (1.23 gm) followed by pyridine (0.964 gm). The mixture was stirred at room temperature overnight. After the usual work up and column purification (hexane-ethyl acetate (1:1), the product was obtained in pure form (700 mg).

$^1$H NMR (DMSO-d$_6$): δ8.54–8.57 (m, 1H); 8.13 (s, 1H); 7.66–7.74 (m, 1H); 7.30–7.45 (m, 12H); 6.91 (s, 1H); 5.49 (s, 1H); 5.32 (dd, 1H, J$_1$=1.0 Hz, J$_2$=3.0 Hz); 5.24 (s, 2H); 3.75 (dd, 1H, J$_1$=4.5 Hz, J$_2$=16.6 Hz); 3.34 (dd, 1H, J$_1$=1.0 Hz, J$_2$=16.6 Hz); 1.31 (s, 3H).

EXAMPLE 35

Preparation of sodium (2S, 3R, 5R)-3-formyl-3-methyl-7-oxo-4-thia-1-azabicyclo[3.2.0]heptane-2-carboxylate, 3$^1$-[O-[(pyridin-2-yl)methyl]oxime], 4,4-dioxide (compound 35)

To a solution of compound 34 (410 mg) in 98% ethanol (25 ml), was added 10% Pd/C (410 mg) and the mixture was hydrogenated for 6 h. The catalyst was removed by filtration through Celite and the filtrate was concentrated to dryness under reduced pressure. The residue was digested with hexane followed by a mixture of hexane-ether (1:1). The precipitated solid was collected by filtration. The solid was suspended in water (10 ml), NaHCO$_3$ (90 mg) was added and stirred at room temperature for 0.5 h. After purification by reverse phase preparative tlc (acetonitrile-water, 8:1), two components were obtained. The minor component (20 mg) was sodium (2S, 3R, 5R)-3-formyl-3 -methyl-7-oxo-4-thia-1-azabicyclo[3.2.0]heptane-2 -carboxylate, 3$^1$-[O-[(pyridin-2 -yl) methyl]oxime], 4,4-dioxide (compound 35).

$^1$H NMR (DMSO-d$_6$): δ8.56 (d, 1H); 7.78–7.86 (m, 1H,); 7.72 (s, 1H); 7.34–7.43 (m, 2[t]); 5.20 (s, 2H); 5.04 (br, d, 1H); 4.36 (s, 1H); 3.56 (dd, 1H, J$_1$=4.0 Hz, J$_2$=16.0 Hz); 3.15 (dd, 1H, J$_1$=1.0 Hz, J$_2$=16.1 Hz); 1.52 (s, 3H).

EXAMPLE 36

Sodium (2S, 3R, 5R)-3-formyl-3 -methyl-7-oxo-4-thia-1-azabicyclo [3.2.0]heptane-2-carboxylate, 3$^1$-[O-[(piperidin-2-yl)methyl]oxime], 4,4-dioxide (compound 36)

The major component from the Example 35 was sodium (2S, 3R, 5R)-3-formyl-3-methyl-7-oxo-4 -thia-1-azabicyclo [3.2.0]heptane-2-carboxylate, 3$^1$-[O-[(piperidin-2-yl) methyl]oxime]4,4-dioxide (80 mg).

$^1$H NMR (D$_2$O): δ7.76 (d, 1H, J=2.2 Hz); 5.11 (br, d, 1H); 4.79 (s, 1H); 4.18–4.45 (m, 2H); 3.49 (dd, 1H, J$_1$=4.2 Hz, J$_2$=16.8 Hz); 3.38–3.61 (br, m, overlapped with a d, 3H, J=16.8 Hz); 2.99 (t, 1H, J=9.0 Hz); 1.46–1.89 (m, overlapped with a s, 9H).

EXAMPLE 37

Preparation of diphenylmethyl (2S, 3R, 5R)-3-formyl-3-methyl-7-oxo-4-thia-1-azabicyclo[3.2.0]heptane-2-carboxylate, 3$^1$-(acetylhydrazone), 4,4-dioxide (compound 37)

To a stirred solution of aldehyde (compound 1, 1.2 gm, 2.9 mmol) in a mixture of ethanol (15 ml) and methylene chloride (15 ml), was added acetic hydrazide (221 mg, 2.9 mmol) followed by 2 drops of conc. HCl. The mixture was stirred at room temperature for 14 h; solvent was removed under reduced pressure and the residue was taken up in methylene chloride (100 ml), washed with water, brine, and dried (Na$_2$SO$_4$).

$^1$H NMR (DMSO-d$_6$): δ11.69 (s, 1H); 7.56 (s, 1H); 7.30–7.50 (m, 10H); 6.90 (s, 1H); 5.77 (s, 1H); 5.34 (br, d, 1H); 3.75 (dd, 1H, J$_1$= 3.0 Hz, J$_2$=16.1 Hz); 3.50 (dd, 1H, J$_1$=1.2 Hz, J$_2$=16.0 Hz); 2.0 (s, 3H); 1.39 (s, 3H).

EXAMPLE 38

Preparation of sodium (2S, 3R, 5R)-3-formyl-3-methyl-7-oxo-4-thia-1-azabicyclo[3.2.0]heptane-2-carboxylate, 3$^1$-(acetylhydrazone), 4,4-dioxide (compound 38)

A solution of the compound 37 (Example 37, 320 mg, 0.68 mmol) in a mixture of ethanol (12 ml) and ethyl acetate (18 ml), was hydrogenated over 10% Pd/C (350 mg) at 50 psi for 8 h. The catalyst was removed by filtration and the filtrate was concentrated under reduced pressure. The residue was digested with a mixture of ether-hexane (1:1). The precipitated solid was filtered off and air-dried. The solid thus obtained was suspended in water (10 ml). NaHCO$_3$ (57 mg) was added and stirred at room temperature for 0.5 h. The resulting mixture was freeze-dried and purified by reverse phase preparative tlc using acetonitrile-water (7:1).

$^1$H NMR (D$_2$O): δ7.69 (s, 1H); 5.13 (br, d, 1H); 4.88 (s, 1H); 3.73 (dd, 1H, J$_1$=3.0 Hz, J$_2$=16.0 Hz); 3.40 (dd, 1H, J$_1$=1.0 Hz, J$_2$=16.0 Hz); 2.12 (s, 3H); 1.71 (s, 3H).

EXAMPLE 39

Preparation of diphenylmethyl (2S, 3R, 5R)-3-methyl-7-oxo-3-[N-(2-oxo-1-imidazolidinyl) formimidoyl]-4 -thia-1-azabicyclo[3.2.0]heptane-2-carboxylate, 4,4-dioxide (compound 39)

To a stirred solution of aldehyde (compound 1, 600 mg, 1.21 mmol) in a mixture of methylene chloride (10 ml) and ethanol (10 ml), was added 1-amino-2-oxo-imidazolidine (122.3 mg, 1.21 mmol) fault by 1 drop of conc. HCl. The mixture was stirred at room temperature for 18 h. The solvent was removed under reduced pressure and the residue was dissolved in a mixture of methylene chloride-ethyl acetate (1:1) and washed successively with water, brine, dried (Na$_2$SO$_4$) and concentrated under reduced pressure. The residue was purified by silica gel column chromatography using hexane-ethyl acetate (4:1) as eluant to afford the product as a foam (190 mg), 26% yield.

$^1$H NMR (CDCl$_3$): δ7.23–7.40 (m, 10H); 6.95 (s, 1H); 6.89 (s, 1H); 5.40–5.62 (br, m, 1H); 5.05 (s, 1H); 4.69 (br, t, 1H); 3.55–3.80 (m, 4H); 3.42–3.55 (m, 2H); 1.52 (s, 3H).

EXAMPLE 40

A solution of compound 39 (190 mg, 0.382 mmol) in ethanol (20 ml) was hydrogenated over 10% Pd/C (200 mg) at 50 psi for 2.5 h. The catalyst was removed by filtration through Celite and the solvent was removed under reduced pressure. The residue was suspended in water (10 ml). NaHCO$_3$ (40 mg) was added and stirred at room temperature for 0.5 h. After freeze-drying, the product was purified by preparative tlc (17 mg, 12%).

$^1$H NMR (D$_2$O): δ6.97 (s, 1H); 5.10 (dd, 1H, J$_1$=1.6 Hz, J$_2$=4.0 Hz); 4.77 (s, 1H); 3.50–3.88 (m, 5H); 3.40 (dd, 1H, J$_1$=1.6 Hz, J$_2$=16.6 Hz); 1.69 (s, 3H).

EXAMPLE 41

Preparation of diphenylmeythyl (2S, 3R, 5R)-3-formyl-3-methyl-7-oxo-4-thia-1-azabicylco[3.2.0]heptane-2-carboxylate, 3$^1$-(benzoyhydrazone), 4,4-dioxide (compound 41)

To a stirred solution of the aldehyde (compound 1, 0.8 gm, 1.94 mmol) in a mixture of methylene chloride (8 ml) and ethanol (15 ml), was added benzoic hydrazide (0.263 gm, 1.94 mmol) followed by 3 drops of conc. HCl. The mixture was stirred at room temperature for 20 h and concentrated under reduced pressure. After the usual work up and column purification over a silica gel column, the desired product was obtained in 51% yield (0.53 gm).

$^1$H NMR (DMSO-d$_6$): δ8.07 (s, 1H); 7.28–8.04 (m, 16H); 6.88 (s, 1H); 5.40 (br, s, 1H); 5.31 (s, 1H); 3.79 (dd, 1H, J$_1$=4.0 Hz, J$_2$=16.0 Hz); 3.36 (dd, 1H, J$_1$=1.0 Hz, J$_2$=16.0 Hz); 1.47 (s, 3H).

EXAMPLE 42

Preparation of sodium (2S, 3R, 5R)-3-formyl-3-methyl-7-oxo-4-thia-1-azabicyclo[3.2.0]heptane-2-carboxylate, 3$^1$-(benzoylhydrazone), 4,4-dioxide (compound 42)

To a solution of the ester (compound 41, 310 mg, 0.58 mmol) in a mixture of ethyl acetate (4 ml) and ethanol (16 ml), was added 10% Pd/C (350 mg). The mixture was hydrogenated at 50 psi for 8 h. The catalyst was removed by filtration through Celite and the filtrate was concentrated under reduced pressure. The residue was digested with ether, and the precipitated solid was collected by filtration and air dried (170 mg). The acid (160 mg) thus obtained was suspended in water (10 ml), sodium bicarbonate (41 mg) was added and the mixture was stirred at room temp. for 30 min, then freeze-dried. The product was purified by reverse phase prep. tlc using a mixture of CH$_3$CN:H$_2$O (8:1). The pure compound was obtained in 59% yield (100 mg).

¹H NMR (DMSO-d₆): δ7.80–8.05 (m, 3H); 7.40–7.60 (m, 4H); 5.07 (br, s, 1H); 4.30 (br, s, 1H); 3.58 (dd, 1H, $J_1$=3.0 Hz, $J_2$=16.0 Hz); 3.17 (dd, 1H, $J_1$=1.0 Hz, $J_2$=16.1 Hz); 1.19 (s, 3H).

EXAMPLE 43

Preparation of diphenylmethyl (2S, 3R, 5R)-3-formyl-3-methyl-7-oxo-4-thia-1-azabicyclo[3.2.0]heptane-2-carboxylate, 3¹-thiosemicarbazone, 4,4-dioxide (compound 43)

To a stirred solution of penam aldehyde (compound 1, 1.7 gm, 4.11 mmol) in a mixture of ethanol (15 ml) and methylene chloride (30 ml), was added thiosemicarbazide (0.375 gm, 4.11 mmol) followed by two drops of conc. HCl. The mixture was stirred at room temp. for 20 h and concentrated under reduced pressure. The residue was dissolved in methylene chloride, washed successively with water, dil. HCl, water, sodium bicarbonate solution, brine, dried (Na₂SO₄) and evaporated to give a viscous mass which was purified over a silica gel column using a mixture of hexane-ethyl acetate as eluant (3:2). The pure compound was obtained in 45% yield (900

¹H NMR (DMSO-d₆): δ11.75 (br, s, 1H, exchanged with D₂O): 8.41 (br, s, 1H, exchanged with D₂O); 8.06 (br, s, 1H, exchanged with D2O) 7.46 (s, 1H); 7.20–7.40 (m, 10H); 6.80 (s, 1H); 5.45 (s, 1H); 5.25 (br, d, 1H, J=2.5 Hz); 3.65 (dd, 1H, $J_1$=4.4 Hz, $J_2$=16.1 Hz); 3.22 (dd, 1H, $J_1$=1.0 Hz, $J_2$=16.0 Hz); 1.35 (s, 3H).

EXAMPLE 44

Preparation of sodium (2S, 3R, 5R)-3-formyl-3-methyl-7-oxo-4-thia-1-azabicyclo[3.2.0]heptane-2-carboxylate, 3¹-thiosemicarbazone, 4,4-dioxide (compound 44)

A mixture of compound 43 (300 mg) in ethanol (25 ml) and 10% Pd/C (600 mg) was hydrogenated at 50 psi for 20 h. After filtration through Ceilte, the filtrate was concentrated under reduced pressure. The residue was digested with ether to afford a solid. The solid (160 mg) was suspended in water (8 ml), NaHCO₃ (47 mg) was added and the mixture was stirred at room temp. for 30 min. The remaining solid was removed by filtration through filter paper and the filtrate was concentrated to a small volume and purified by reverse phase preparative tlc using acetonitrile-water (7:1) as solvent system. After freeze-drying, the product was obtained in 18% yield (38 mg).

¹H NMR (DMSO-d₆): δ11.05 (br, s, 1H); 7.93 (br, s, 1H); 7.61 (s, 1H); 7.44 (br, s, 1H); 6.51 (s, 1H); 4.20 (br, d, 1H); 3.10 (br, d, 1H, J=14.9 Hz); 2.80 (dd, 1H, $J_1$=3.2 Hz, $J_2$=15.0 Hz); 1.90 (s, 3H).

EXAMPLE 45

Preparation of diphenylmethyl(2s, 3R, 5R)-3-formyl-3-methyl-7-oxo-4-thia-1-azabicyclo[3.2.0]heptane-2-carboxylate, 3¹-semicarbazone, 4,4-dioxide (compound 45)

To a stirred solution of the penam aldehyde (compound 1, 2.3 gm, 5.6 mmol) in a mixture of ethanol (10 ml) and methylene chloride (10 ml), was added semicarbazide hydrochloride (0.477 gm, 4.3 mmol) followed by pyridine (0.204 gm, 2.58 mmol). The mixture was stirred at room temp. for 14 h. Solvent was removed under reduced pressure and the residue was taken up in methylene chloride, washed successively with water, brine, dried (Na₂SO₄) and evaporated under reduced pressure to give a solid (2.4 gm). The product was purified by silica gel column chromatography using a mixture of hexane-ethyl acetate (1:1) to give the pure product (480 mg).

¹H NMR (DMSO-d₆): δ10.67 (s, 1H); 7.25–7.48 (m, 10H); 6.92 (s, 1H); 6.61 (br, s, 2H); 5.39 (s, 1H); 5.33 (br, d, 1H, J=2.90 Hz); 3.73 (dd, 1H, $J_1$=4.5 Hz, $J_2$=16.5 Hz); 3.34 (dd, 1H, $J_1$=1.0 Hz, $J_2$=16.5 Hz); 1.43 (s, 3H).

EXAMPLE 46

Preparation of sodium (2S, 3R, 5R)-3-formyl-3-methyl-7-oxo-4-thia-1-azabicyclo[3.2.0]heptane-2-carboxylate, 3¹-semicarbazone, 4,4-dioxide (compound 46)

This compound was prepared in the same manner as described for compound 44. Thus, a solution of compound 45 (380 mg, 0.81 mmol) in a mixture of ethanol (15 ml) and ethyl acetate (15 ml) was hydrogenated over 10% Pd/C at 50 psi for 24 h. The reaction mixture was filtered through a bed of Celite and the filtrate was concentrated under reduced pressure. The residue was digested with ether and the precipitated solid was collected by filtration and air dried (240 mg). The acid thus obtained was suspended in 10 ml of water. 68 mg of NaHCO₃ was added and the mixture was stirred at room temp. for 30 min and filtered through filter paper. The filtrate was concentrated under reduced pressure to a small volume which was purified by reverse phase preparative tlc using acetonitrile-water (7:1) as developing solvent. After freeze-drying, the product was obtained as a fluffy solid, 126 mg (62%).

¹H NMR (DMSO-d₆): δ10.42 (br, s, 1H); 7.22 (s, 1H); 6.33 (br, s, H); 4.97 (br, s, 1H); 4.19 (s, 1H); 3.53 (dd, 1H, $J_1$=4.0 Hz, $J_2$=16.0 Hz); 3.10 (dd, 1H, $J_1$=1.0 Hz, $J_2$=15.9 Hz); 1.52 (s, 3H).

EXAMPLE 47

Preparation of diphenylmethyl (2s, 3R, 5R)-3-formyl-3-methyl-7-oxo-4-thia-1-azabicyclo[3.2.0]heptane-2-carboxylate, 3¹-(benzyloxycarbonylhydrazone), 4,4-dioxide (compound 47)

To a stirred solution of the penam aldehyde (compound 1, 2.0 gm, 4.84 mmol) in a mixture of ethanol (40 ml) and methylene chloride (40 ml), was added N-benzyloxycarbonyl-hydrazine hydrochloride (891 mg, 4.3978 mmol) followed by pyridine (313 mg, 320 μl). The mixture was stirred at room temp. for 8 h. After usual work up and column purification over a silica gel column (hexane-ethyl acetate, 2:1), the product was obtained as a foam (745 mg) in 27% yield.

¹H NMR (DMSO-d₆): δ11.75 (br, s, 1H); 7.61 (s, 1H); 7.22–7.41 (m, 15H); 6.87 (s, 1H); 5.20–5.40 (m, 4H); 3.75 (dd, 1H, $J_1$=4.7 Hz, $J_2$=16.6 Hz); 3.32 (dd, 1H, $J_1$=1.0 Hz, $J_2$=16.6 Hz); 1.38 (s, 3H).

EXAMPLE 48

Preparation of sodium (2S, 3R, 5R)-3-formyl-3-methyl-7-oxo-4-thia-1-azabicyclo[3.2.0]heptane-2-carboxylate, 3¹-(benzyloxycarbonylhydrazone), 4,4-dioxide (compound 48)

After catalytic hydrogenation and usual work up the title compound was obtained as white fluffy solid (26 mg) in 12% yield.

¹H NMR (DMSO-d₆): δ11.34 (br, s, 1H); 7.23–7.45 (m, 5H); 5.11 (s, 2H); 4.97 (br, d, 1H, J=2.9 Hz); 4.15 (s, 1H); 3.52 (dd, 1H, $J_1$=3.9 Hz, $J_2$=16.0 Hz); 3.10 (dd, 1H, $J_1$=1.0 Hz, $J_2$=16.0 Hz); 1.50 (s, 3H).

EXAMPLE 49

Preparation of diphenylmethyl (2S, 3R, 5R)-3-formyl-3-methyl-7-oxo-4-thia-1-azabicyclo[3.2.0]heptane-2- carboxylate, $3^1$-(trichloroethyloxycarbonylhydrazone), 4,4-dioxide (compound 49)

This compound was prepared in the same manner as described for compound 47; trichloroethyloxycarbonyl hydrazine hydrochloride was used. After usual work up and purification over a silica gel column, the title compound was obtained in 36% yield.

$^1$H NMR (DMSO-$d_6$): $\delta$12.18 (br, s, 1H); 7.72 (s, 1H); 7.25–7.47 (m, 10H); 6.89 (s, 1H); 5.30–5.40 (d, overlapped with a s, 2H); 5.00 (s, 2H); 3.76 (dd, 1H, $J_1$=4.4 Hz, $J_2$=16.2 Hz); 3.32 (dd, 1H, $J_1$=1.0 Hz, $J_2$=16.2 Hz); 1.39 (s, 3H).

EXAMPLE 50

Preparation of diphenylmethyl (2S, 3R, 5R)-3-formyl-3-methyl-7-oxo-4-thia-1-azabicyclo[3.2.0]heptane-2-carboxylate, $3^1$-(2-methyl-3-thiosemicarbazone), 4,4-dioxide (compound 50)

This compound was prepared in the same manner as described for compound 43. In place of thiosemicarbazide, 2-methyl-3-thiosemicarbazide was used. After usual work up and column purification the title compound was obtained in 27% yield.

$^1$H NMR (DMSO-$d_6$): $\delta$8.69 (br, s, 1H); 8.10 (br, s, 1H); 7.53 (s, 1H); 7.20–7.45 (m, 10H); 6.87 (s, 1H); 5.71 (s, 1H); 5.34 (br, d, 1H, J=2.9 Hz); 3.74 (s, 3H); 3.75 (dd, 1H, $J_1$=4.0 Hz, $J_2$=16.1 Hz); 3.34 (dd, 1H, $J_1$=1.0 Hz, $J_2$=16.3 Hz); 1.49 (s, 3H).

EXAMPLE 51

Preparation of diphenylmethyl (2S, 3R, 5R)-3-formyl-3-methyl-7-oxo-4-thia-1-azabicyclo[3.2.0]heptane-2-carboxylate, $3^1$-(nicotinoylhydrazone), 4,4-dioxide (compound 51)

By using nicotinic hydrazide, the compound 51 was prepared from the penam aldehyde (compound 1) in the same manner as described previously.

$^1$H NMR (DMSO-$d_6$) $\delta$9.09 (br, s, 1H); 8.80 (br, d, 1H); 8.30 (br, d, 1H); 8.06 (s, 1H); 7.65 (br, t, 1H); 7.20–7.50 (m, 11H); 6.89 (s, 1H); 5.37 (br, s, 2H); 3.78 (dd, 1H, $J_2$=3.0 Hz, $J_2$=15.5 Hz); 3.34 (dd, 1H, $J_1$=0.9 Hz, $J_2$=15.5 Hz); 1.47 (s, 3H).

EXAMPLE 52

Preparation of diphenylmethyl (2S, 3R, 5R)-3-formyl-3-methyl-7-oxo-4-thia-1-azabicyclo[3.2.0]heptane-2-carboxylate, 3-(2-hydroxybenzoylhydrazone), 4,4-dioxide (compound 52), By using salicyclic hydrazide, the compound 52 was prepared from the penam aldehyde (compound 1) in the same manner as described before for compound 41.

$^1$H NMR (DMSO-$d_6$) :$\delta$12.16 (br,s,1H); 11.50 (br, s,1H); 8.10 (s, 1H); 6.92–7.90 (m,14H); 6.90 (s,1H); 5.40 (d,1H, J=3.8 Hz); 5.35 (s,1H); 3.80 (dd, 1H, $J_1$=3.8 Hz, $J_2$=15.5 Hz); 3.37 (dd,1H, $J_1$=1.0 Hz, $J_2$=15.5 Hz); 1.46 (s, 3H).

The compounds obtained in some of the examples were checked for β-lactamase inhibitory activity and antibacterial activity.

(1) Test for antibacterial activity

The compounds of the present invention, piperacillin or ceftazidime alone, were tested for minimal inhibitory concentration (MIC) against the bacteria listed in Tables (1–3) according to the agar dilution method described below. The MICs of the antibiotics (piperacillin and ceftazidime) in combination with the present compounds (5 μg/ml) were determined with the same bacteria. After incubation in Mueller-Hinton broth (Difco) at 37° C. for 18 h, the bacterial suspension was diluted and about $10^5$ CFU/spot was applied to the drug-containing Mueller-Minton agar (Difco) plates. The MICs were recorded after 18 h of incubation at 37° C. on the lowest combinations of drug that inhibited visible growth of bacteria. In the tables, the present compounds are shown by the compound number and the bacteria used in the test were those capable of producing β-lactamase.

TABLE 1

| | | MIC (μg/ml) | | | | | | | | | | | | | | | | |
|---|---|---|---|---|---|---|---|---|---|---|---|---|---|---|---|---|---|---|
| | Pipera-cillin | Present Compound (Combined with Piperacillin) | | | | | | | | | | | | | | | | |
| Bacterial Strains | Alone | 3 | 5 | 8 | 10 | 12 | 15 | 17 | 19 | 21 | 26 | 28 | 30 | 33 | 36 | 38 | 40 | 42 |
| S. aureus 1628 | 400 | 50 | 200 | 50 | 50 | 100 | 200 | 200 | 100 | 200 | 100 | 100 | 50 | 200 | 200 | 50 | 100 | 50 |
| S. aureus 54K | 12.5 | 0.78 | ≦0.2 | 0.39 | 0.39 | 0.39 | 1.56 | 1.56 | 0.39 | ≦0.2 | 0.39 | 0.78 | 0.39 | 1.56 | 0.39 | 0.39 | 0.78 | 0.39 |
| S. aureus 80K | 12.5 | 0.78 | ≦0.2 | ≦0.2 | ≦0.2 | ≦0.2 | 0.78 | 0.78 | 0.78 | ≦0.2 | 0.39 | ≦0.2 | ≦0.2 | 0.78 | 0.39 | ≦0.2 | 0.78 | ≦0.2 |
| E. coli TEM 1 | 400 | 6.25 | 12.5 | 25 | 12.5 | 25 | 25 | 0.78 | 50 | 0.39 | 50 | 0.78 | 25 | 12.5 | 1.56 | 25 | 50 | 25 |
| E. coli TEM 3 | 100 | 1.56 | 1.56 | 1.56 | 1.56 | 0.78 | 3.13 | 1.56 | 3.13 | 0.78 | 1.56 | 0.78 | 1.56 | 1.56 | 0.78 | 1.56 | 1.56 | 1.56 |
| E. coli TEM 7 | 100 | 0.78 | 6.25 | 0.39 | ≦0.2 | ≦0.2 | 1.56 | 0.39 | 6.25 | ≦0.2 | 0.39 | 0.39 | 0.78 | 0.39 | ≦0.2 | 0.78 | 12.5 | 3.13 |
| E. coli OXA 1 | 25 | 0.78 | 6.25 | 3.13 | 1.56 | 1.56 | 6.25 | 0.78 | 6.25 | 1.56 | 6.25 | 0.78 | 6.25 | 1.56 | 3.13 | 12.5 | 25 | 25 |
| E. coli OXA 3 | 3.13 | 0.78 | 0.78 | 1.56 | 0.78 | 0.39 | 0.78 | 0.39 | 1.56 | 0.78 | 1.56 | 0.78 | 0.78 | 0.78 | 1.56 | 1.56 | 0.78 | 1.56 |
| E. coli SHV 1 | 50 | 0.78 | 0.78 | — | — | 0.39 | 3.13 | 0.39 | 3.13 | ≦0.2 | 1.56 | — | — | 0.39 | ≦0.2 | — | 3.13 | — |
| K. pneumoniae 336L | 200 | 25 | 25 | 50 | 25 | 50 | 50 | 3.13 | 50 | 0.78 | 50 | 1.56 | 50 | 25 | 12.5 | 25 | 100 | 100 |
| K. pneumoniae CTX1 | >40 | 6.25 | 12.5 | 25 | 25 | 12.5 | 400 | 12.5 | 200 | 12.5 | 12.5 | 12.5 | 200 | 12.5 | 25 | 25 | 25 | 100 |
| S. marcescens 200L | 100 | <0.2 | 12.5 | 0.78 | 0.78 | 1.56 | 12.5 | 0.78 | 12.5 | 0.39 | 3.13 | 0.78 | 3.13 | 0.78 | 1.56 | 12.5 | 12.5 | 12. |
| P. vulgaris CT106 | 400 | 1.56 | 100 | 6.25 | 6.25 | 1.56 | 100 | 1.56 | 200 | 3.13 | 25 | 0.78 | 1.56 | 3.13 | 3.13 | 100 | 200 | 200 |
| C. freundii 2046E | 100 | 0.39 | 1.56 | 0.39 | 0.39 | 0.78 | 3.13 | ≦0.2 | 6.25 | ≦0.2 | 1.56 | ≦0.2 | ≦0.2 | ≦0.2 | 0.78 | 3.13 | 12.5 | 25 |
| E. cloacae P99 | 200 | 25 | 200 | 200 | 200 | 25 | 200 | 50 | 100 | 50 | 100 | 200 | 200 | 100 | 200 | 12.5 | 25 | 50 |
| E. cloacae 40011 | 50 | 12.5 | 25 | 50 | 25 | 12.5 | 50 | 12.5 | 50 | 12.5 | 50 | 25 | 50 | 25 | 25 | 3.13 | 6.25 | 6.25 |
| E. cloacae 40015 | 50 | 12.5 | 12.5 | 50 | 50 | 12.5 | 50 | 12.5 | 25 | 12.5 | 25 | 25 | 50 | 25 | 25 | 25 | 12.5 | 25 |
| E. cloacae E. 4009 | 100 | 12.5 | 50 | 100 | 100 | 12.5 | 100 | 50 | 100 | 25 | 50 | 100 | 100 | 100 | 100 | 3.13 | 6.25 | 25 |

TABLE 1-continued

| | Pipera-cillin | Present Compound (Combined with Piperacillin) | | | | | | | | | | | | | | | |
|---|---|---|---|---|---|---|---|---|---|---|---|---|---|---|---|---|---|
| Bacterial Strains | Alone | 3 | 5 | 8 | 10 | 12 | 15 | 17 | 19 | 21 | 26 | 28 | 30 | 33 | 36 | 38 | 40 | 42 |
| E. aerogenes | 25 | 6.25 | 12.5 | 25 | 25 | 12.5 | 25 | 12.5 | 25 | 12.5 | 12.5 | 25 | 25 | 25 | 25 | 6.25 | 3.13 | 12.5 |
| E. aerogenes 41004 | 25 | 6.25 | 12.5 | 25 | 25 | 12.5 | 25 | 12.5 | 25 | 12.5 | 25 | 25 | 25 | 25 | 25 | 3.13 | 6.25 | 12.5 |
| P. aeruginosa L 46007 | 100 | 50 | 25 | 25 | 25 | 25 | 50 | 25 | 50 | 25 | 50 | 12.5 | 25 | 50 | 25 | 25 | 50 | 12.5 |
| M. morganii 36010 | 200 | 6.25 | 100 | 100 | 25 | 12.5 | 200 | 25 | 100 | 6.25 | 100 | 25 | 100 | 100 | 100 | 50 | 200 | 100 |
| M. morganii 36014 | 50 | ≦0.2 | 12.5 | 0.78 | 0.39 | ≦0.2 | 25 | ≦0.2 | 6.25 | 0.39 | 3.13 | 0.78 | 25 | 1.56 | 6.25 | ≦0.2 | 1.56 | 1.56 |
| A. calcoaceticus 553L | >400 | 25 | 100 | 50 | 50 | 50 | 100 | 12.5 | 100 | 12.5 | 50 | 25 | 50 | 100 | 25 | 100 | 200 | 200 |

TABLE 2

| | Ceftazidime | Present Compound (combined with ceftazidime) | | | | | | | | |
|---|---|---|---|---|---|---|---|---|---|---|
| Bacterial Strains | (Alone) | 3 | 5 | 8 | 10 | 12 | 15 | 17 | 19 | 21 |
| E. coli TEM-3 | 25 | 0.39 | 0.78 | 0.78 | 0.39 | 0.39 | 0.78 | 0.39 | 3.13 | 0.39 |
| E. coli TEM-7 | 25 | 0.39 | 12.5 | 1.56 | 0.39 | ≦0.2 | 1.56 | 0.39 | 6.25 | 0.78 |
| K. pneumoniae CTX-1 | 100 | 1.56 | 1.56 | 3.13 | 1.56 | 1.56 | 25 | 1.56 | 25 | 1.56 |
| P. vulgaris CT-106 | 12.5 | 0.39 | 3.13 | 1.56 | 0.78 | 0.78 | 6.25 | 0.78 | 12.5 | 0.39 |
| E. cloacae P-99 | 100 | 12.5 | 50 | 50 | 25 | 12.5 | 100 | 25 | 100 | 25 |
| P. aeruginosa 46220 DR-2 | 25 | 12.5 | 25 | 25 | 25 | 12.5 | 12.5 | 6.25 | 12.5 | 12.5 |
| E. cloacae 40011 | 50 | 6.25 | 25 | 50 | 25 | 12.5 | 25 | 6.25 | 50 | 25 |
| E. aerogenes 41003 | 25 | 3.13 | 12.5 | 25 | 12.5 | 3.13 | 25 | 12.5 | 25 | 12.5 |
| E. aerogenes 41004 | 25 | 3.13 | 12.5 | 25 | 12.5 | 6.25 | 25 | 12.5 | 25 | 12.5 |
| P. aeruginosa L 46003 | 200 | 100 | 100 | 200 | 200 | 12.5 | 200 | 50 | 50 | 200 |
| M. morganii 36010 | 200 | 6.25 | 25 | 50 | 25 | 6.25 | 100 | 6.25 | 100 | 12.5 |
| M. morganii 36014 | 25 | ≦0.2 | 3.13 | 3.13 | 0.78 | ≦0.2 | 12.5 | ≦0.2 | 6.25 | ≦0.2 |

TABLE 3

| | Ceftazidime | Present compound (combined with ceftazidime) | | | | | | | |
|---|---|---|---|---|---|---|---|---|---|
| Bacterial Strains | (Alone) | 26 | 28 | 30 | 33 | 36 | 38 | 40 | 42 |
| E. coli TEM-3 | 25 | 0.78 | ≦0.2 | 1.56 | 0.39 | 0.39 | 0.78 | 0.78 | 0.78 |
| E. coli TEM-7 | 25 | 0.78 | 0.39 | 3.13 | ≦0.2 | ≦0.2 | 1.56 | 3.13 | 3.13 |
| K. pneumoniae CTX-1 | 100 | 3.13 | 0.78 | 12.5 | 1.56 | 3.13 | 1.56 | 1.56 | 6.25 |
| P. vulgaris CT 106 | 12.5 | 1.56 | 0.39 | 0.39 | 1.56 | 0.78 | 6.25 | 12.5 | 6.25 |
| E. cloacae P99 | 100 | 100 | 12.5 | 100 | 100 | 50 | 6.25 | 6.25 | 6.25 |
| P. aeruginosa 46220 DR-2 | 25 | 12.5 | 25 | 12.5 | 12.5 | 25 | 12.5 | 25 | 12.5 |
| E. cloacae 40011 | 50 | 50 | 50 | 50 | 25 | 50 | 3.13 | 3.13 | 6.25 |
| E. cloacae E. 40009 | 100 | 100 | 50 | 100 | 50 | 100 | 6.25 | 12.5 | 12.5 |
| E. aerogenes 41003 | 25 | 12.5 | 25 | 25 | 25 | 25 | 6.25 | 3.13 | 6.25 |
| E. aerogenes 41004 | 25 | 12.5 | 25 | 25 | 12.5 | 12.5 | 6.25 | 3.13 | 6.25 |
| E. aerogenes 41006 | 100 | 50 | 100 | 100 | 50 | 100 | 25 | 12.5 | 25 |
| M. morganii 36010 | 200 | 50 | 50 | 200 | 25 | 25 | 25 | 100 | 100 |
| M. morganii 36014 | 25 | 3.13 | 0.78 | 25 | 1.56 | 3.13 | ≦0.2 | 1.56 | 1.56 |

(2) Test for β-lactamase inhibitory activity.

The inhibitory activities of present compounds against TEM-1 (isolated from E. coli), CTX-1 (isolated from K. pneumoniae), cephalosporinase (isolated from P. aeruginoase 46012) was measured by spectrophotometric rate assay using 490 nM and using nitrocefin as a substrate [J. Antimicrob. Chemother., 28, pp. 775–776 (1991)]. Table 4 shows the results.

TABLE 4

| | 50% Inhibitory conc., μM | | |
|---|---|---|---|
| Compound | TEM-1 | CTX-1 | Cephalosporinase |
| Compound 3 | 0.3 | 0.006 | 1.9 |
| Compound 5 | 0.58 | 0.02 | 7.0 |
| Compound 8 | 0.1 | 0.001 | 1.0 |
| Compound 10 | 0.5 | 0.005 | 1.0 |
| Compound 28 | 0.0048 | 0.0025 | 1.0 |
| Compound 38 | 0.0014 | 0.1 | 0.6 |

Given below are examples of preparation of the present antibacterial compositions.

Preparation Example 1

| | |
|---|---|
| Piperacillin | 200 mg |
| Compound 3 | 200 mg |
| Lactose | 100 mg |
| Crystalline cellulose | 57 mg |
| Magnesium stearate | 3 mg |
| Total | 560 mg (amount per capsule) |

The above ingredients are formulated in the proportions listed above into a capsule.

Preparation Example 2

| | |
|---|---|
| Piperacillin | 100 mg |
| Compound 38 | 100 mg |
| Lactose | 300 mg |
| Cornstarch | 490 mg |
| Hydroxypropyl methyl cellulose | 10 mg |
| Total | 1000 mg (amount per dose) |

The above ingredients are formulated in the proportions listed above into granules.

Preparation Example 3

| | |
|---|---|
| Compound 3 | 120 mg |
| Hydroxypropyl cellulose | 3 mg |
| Cornstarch | 25 mg |
| Magnesium stearate | 2 mg |
| Total | 150 mg (amount per tablet) |

The above ingredients are formulated in the proportions listed above into a tablet.

We claim:

1. A compound of formula I or Ia wherein $R_1$ is the residue of a carboxy protecting group;

$R_a$ is hydrogen or a pharmaceutically-acceptable salt forming agent or a pharmaceutically acceptable ester residue readily hydrolyzable in vivo;

$R_2$ is $OR_3$ or $NR_4R_5$, wherein $R_3$ is selected from the group consisting of: (a) hydrogen; (b) straight or branched chain alkyl having from 1 to 20 carbon atoms; (c) alkenyl having from 2 to 20 carbon atoms; (d) alkynyl having from 2 to 20 carbon atoms; (e) cycloalkyl having from 3 to 8 carbon atoms; (f) cycloalkenyl having from 5 to 8 carbon atoms; (g) benzyl and (h) a heterocyclic alkyl wherein the heterocyclic group means a 5-(or 6-) membered ring containing from 1 to 4 of any one or more of the heteroatoms selected from O, S and N; (b) to (h) can be unsubstituted or substituted by radicals selected from the group consisting of alkyl, hydroxy, alkoxy, alkanoyloxy, halo, cyano, azido, nitro, carboxy, alkoxycarbonyl, alkanoyl, amino, substituted amino, amidino, guanidino, carboxamido, substituted carboxamido, mercapto, sulfinyl, sulfonyl, diethoxyphosphinylalkyl, dihydroxyphosphinylalkyl, a heteroarylthio, a heteroaryl group bonded via carbon, [or]and a nitrogen containing heterocyclic group bonded via nitrogen;

wherein $R_4$ is selected from the group consisting of: (a) hydrogen; (b) straight or branched chain lower alkyl; (c) cycloalkyl; (d) alkanoyl; (e) benzoyl; (f) amido; (g) thioamido; (h) amidino; (i) benzyloxycarbonyl; and (j) trichloroethyloxycarbonyl;

$R_5$ is hydrogen or any of the groups (b) to (j) defined for $R_4$; and $R_4$ and $R_5$ may join together and form part of [the]a heterocyclic group which may contain one or more additional heteroatoms selected from N, S or O; and the pharmaceutically-acceptable salts thereof and the pharmaceutically-acceptable and readily hydrolyzable esters thereof.

2. The compound of claim 1 wherein the heterocyclic group

, is selected from the group consisting of wherein R is hydrogen, lower alkyl, carboxy (including salt), alkoxycarbonyl, carboxymethyl (including salt), or alkoxycarbonylmethyl and n=0,1,2.

3. The compound of claim 1 wherein $R_1$ can be removed without cleaving the β-lactam ring, and is sufficiently stable under the reaction conditions to permit easy access to the compound of formula (Ia) by de-esterification.

4. The compound of claim 1 wherein $R_1$ is selected from the group consisting of benzyl, diphenylmethyl, 4-nitrobenzyl, 4-methoxybenzyl, allyl, t-butyl, methoxymethyl, tetrahydropyranyl, 2,2,2-trichloroethyl, and trimethylsilyl.

5. The compound of claim 1 wherein $R_3$ is selected from the group consisting of hydrogen, methyl, ethyl, propyl, butyl, t-butyl, allyl, propargyl, iso-propyl, cyclopentyl, cyclopropylmethyl, $-CH_2COOC_2H_5$, $-CH_2COOH$, $-CH_2COOBu^t$, hydroxyethyl, cyanomethyl, nitromethyl, aminoethyl, guanidinoethyl, amidinomethyl, amidinoethyl, bromoethyl, carboxamidomethyl, substituted carboxamidomethyl, methoxymethyl, benzyl, thienylmethyl, furylmethyl, pyridylmethyl, azidoethyl, 1,2,3-triazol-1-yl ethyl, 2methyl-1,3,4-thiadiazol-5-yl-thioethyl and 1-methyl-1,2,3,4-tetrazol-5-yl thioethyl.

6. The compound of claim 1 wherein $R_4$ and $R_5$ are same or different, and are selected from the group consisting of hydrogen; lower alkyl; acetyl; benzoyl; amido; thioamido; amidino; benzyloxycarbonyl; trichloroethyloxycarbonyl; and heteroaroyl.

7. A pharmaceutical composition suitable for the treatment of bacterial infections in mammals comprising the compound of claim 1 and a pharmaceutically acceptable excipient.

8. A method of treating bacterial infections comprising administering to a subject in need of such treatment an effective amount of a β-lactam antibiotic and a compound of claim 1.

9. The method of claim 8 wherein the β-lactam antibiotic and the compound of claim 1 are administered simultaneously.

10. The method of claim 8 wherein the β-lactam antibiotic and the compound of claim 1 are administered separately.

11. The method of claim 8 wherein the β-lactam antibiotic is selected from the group consisting of amoxicillin, ampicillin, azlocillin, mezlocillin, apalcillin, hetacillin, bacampicillin, carbenicillin, sulbenicillin, ticarcillin, piperacillin, mecillinam, methicillin, ciclacillin, talampicillin, cephalothin, cephaloridine, cefaclor, cefadroxil, cefamandole, cefazolin, cephalexin, cephradine, cephapirin, cefuroxime, cefoxitin, cephacetrile, cefotiam, cefotaxime, cefatriazine, cefsulodin, cefoperazone, ceftizoxime, cefmenoxime, cefmetazole, cephaloglycin, cefonicid, cefodizime, cefpirome, ceftazidime, cefpiramide, ceftriaxone, and cefbuperazone.

12. A method for making the compound of formula (I) according to claim 1 comprising:

a) providing a compound of formula (II);

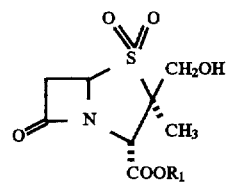

b) oxidizing the compound of a) with an oxidant to form a compound of formula (III);

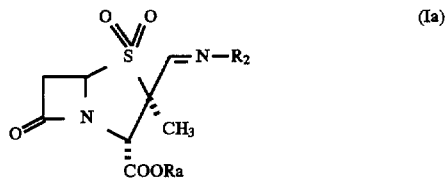

c) reacting the compound of formula III with either
(i) a hydroxylamine derivative or its salt, to form a compound of formula I wherein $R_2$ is $OR_3$; or
(ii) a hydrazine derivative or its salt, to form a compound of formula I wherein $R_2$ is $NR_4R_5$; and d) purifying the desired product.

13. A method of making a compound of formula (Ia) according to claim 1 comprising de-esterifying a compound of formula (I), to obtain a derivative of the formula (Ia) in which $R_a$ is hydrogen.

14. A compound of formula Ia

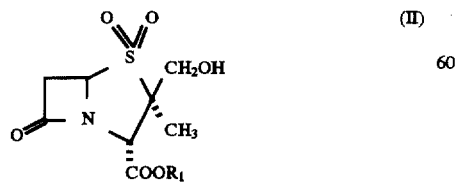

wherein $R_a$ is hydrogen or a pharmaceutically-acceptable salt forming agent or a pharmaceutically acceptable ester residue readily hydrolyzable in vivo;

$R_2$ is $OR_3$ or $NR_4R_5$, wherein $R_3$ is selected from the group consisting of: (a) hydrogen; (b) straight or branched chain alkyl having from 1 to 20 carbon atoms; (c) alkenyl having from 2 to 20 carbon atoms; (d) alkynyl having from 2 to 20 carbon atoms; (e) cycloalkyl having from 3 to 8 carbon atoms; (f) cycloalkenyl having from 5 to 8 carbon atoms; (g) benzyl and (h) a heterocyclic alkyl wherein the heterocyclic group means a 5-(or 6-) membered ring containing from 1 to 4 of any one or more of the heteroatoms selected from O, S and N; (b) to (h) can be unsubstituted or substituted by radicals selected from the group consisting of alkyl, hydroxy, alkoxy, alkanoyloxy, halo, cyano, azido, nitro, carboxy, alkoxycarbonyl, alkanoyl, amino, substituted amino, amidino, guanidino, carboxamido, substituted carboxamido, mercapto, sulfinyl, sulfonyl, diethoxyphosphinylalkyl, dihydroxyphosphinylalkyl, a heteroarylthio, a heteroaryl group bonded via carbon, or a nitrogen containing heterocyclic group bonded via nitrogen;

wherein $R_4$ is selected from the group consisting of: (a) hydrogen; (b) straight or branched chain lower alkyl; (c) cycloalkyl; (d) alkanoyl; (e) benzoyl; (f) amido; (g) thioamido; (h) amidino; (i) benzyloxycarbonyl; and (j)trichloroethyloxycarbonyl;

$R_5$ is hydrogen or any of the groups (b) to (j) defined for $R_4$; and $R_4$ and $R_5$ may join together and form part of the heterocyclic group $-N\bigcirc$ which may contain one or more additional heteroatoms selected from N, S or O; and the pharmaceutically-acceptable salts thereof and the pharmaceutically-acceptable and readily hydrolyzable esters thereof, which compound contains variable amounts of water.

* * * * *

UNITED STATES PATENT AND TRADEMARK OFFICE
CERTIFICATE OF CORRECTION

PATENT NO. : 5,686,441

DATED : November 11, 1997

INVENTOR(S) : Maiti et al.

It is certified that error appears in the above-identified patent and that said Letters Patent is hereby corrected as shown below:

Column 1, line 16, delete "infecticn" insert therefor -- infection --.

Column 8, line 11, after "Lewis acid" insert -- (e.g., --.

Column 11, line 19, delete "preparation" insert therefor -- Preparation --.

Column 11, line 57, delete "$J_2$=1.2 Hz" insert therefor -- $J_1$=1.2 Hz --.

Column 15, line 3, delete "D2O" insert therefor -- $D_2O$ --.

Column 15, line 53, delete "$m_9$)" insert therefor -- mg) --.

Column 15, line 56, delete "D2O" insert therefor -- $D_2O$ --.

Column 15, line 63, delete "methy1" insert therefor -- methyl --.

Column 16, line 11, delete "6.92 (s, 1H" insert therefor -- 6.92(s, 1H) --.

Column 18, line 7, delete "(590" insert therefor -- (590 mg). --.

Column 18, line 43, delete "diphenylmlmethyloxyamine"

insert therefor -- diphenylmethyloxycarbonylmethyloxyamine --.

UNITED STATES PATENT AND TRADEMARK OFFICE
CERTIFICATE OF CORRECTION

PATENT NO. : 5,686,441

DATED : November 11, 1997

INVENTOR(S) : Maiti et al.

It is certified that error appears in the above-identified patent and that said Letters Patent is hereby corrected as shown below:

Column 19, line 5, delete "(7:1.5" insert therefor -- (7:1.5) --.

Column 21, line 11, delete "(m,2[t)" insert therefor -- (m,2H) --.

Column 22, line 6, delete "fault" insert therefor -- followed --.

Column 22, after "EXAMPLE 40", insert the following to read as: -- Preparation of Sodium (2S, 3R, 5R)-3-methyl-7-oxo-3-[N-(2-oxo-1-imidazolidinyl)formimidoyl]-4-thia-1-azabicyclo[3.2.0]heptane-2-carboxylate, 4,4-dioxide(compound 40) --.

Column 22, line 36, delete "3[1]-(benzoyhydrazone)" insert therefor -- 3[1]-(benzoylhydrazone) --.

Column 23, line 22, delete "(900" insert therefor -- (900 mg) --.

Column 23, line 25, delete "D2O" insert therefor -- $D_2O$ --.

Column 24, line 34, delete "(2s, 3R, 5R)" insert therefor -- (2S, 3R, 5R) --.

Table 1, last column, line 14, delete "12." insert therefor -- 12.5 --.

Table 1-continued, first column, line 1, after "E. aerogenes" insert -- 41003 --.

Column 28, line 1, delete "noase" insert therefor -- nosa --.

UNITED STATES PATENT AND TRADEMARK OFFICE
CERTIFICATE OF CORRECTION

PATENT NO. : 5,686,441

DATED : November 11, 1997

INVENTOR(S) : Maiti et al.

It is certified that error appears in the above-identified patent and that said Letters Patent is hereby corrected as shown below:

Column 6, correct the structure as indicated below:

Delete                                          Insert therefor

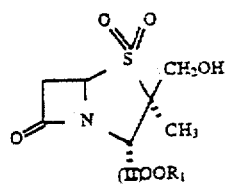   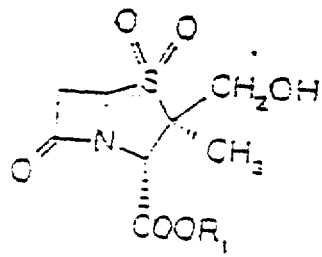

(II)

UNITED STATES PATENT AND TRADEMARK OFFICE
CERTIFICATE OF CORRECTION

PATENT NO. : 5,686,441

DATED : November 11, 1997

INVENTOR(S) : Maiti et al.

It is certified that error appears in the above-identified patent and that said Letters Patent is hereby corrected as shown below:

Column 32, correct the structure as indicated below:

Delete

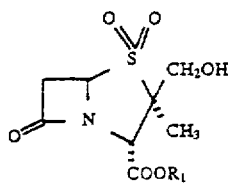 (II)

Insert therefor

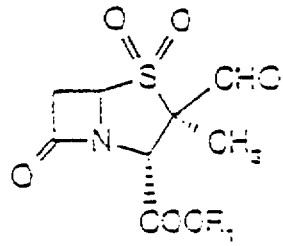 (III)

Signed and Sealed this

Sixteenth Day of March, 1999

Attest:

Q. TODD DICKINSON

Attesting Officer   Acting Commissioner of Patents and Trademarks